(12) United States Patent
Harrison, Jr. et al.

(10) Patent No.: US 11,446,365 B2
(45) Date of Patent: Sep. 20, 2022

(54) ANTIMALARIAL ENZYME CONJUGATES, KITS CONTAINING SAME, AND METHODS OF PRODUCING AND USING SAME

(71) Applicant: The Board of Regents of the University of Oklahoma, Norman, OK (US)

(72) Inventors: Roger G. Harrison, Jr., Norman, OK (US); Patrick H. McKernan, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/331,634

(22) PCT Filed: Aug. 9, 2018

(86) PCT No.: PCT/US2018/045968
§ 371 (c)(1),
(2) Date: Mar. 8, 2019

(87) PCT Pub. No.: WO2020/032951
PCT Pub. Date: Feb. 13, 2020

(65) Prior Publication Data
US 2021/0177948 A1    Jun. 17, 2021

Related U.S. Application Data

(60) Provisional application No. 62/543,172, filed on Aug. 9, 2017.

(51) Int. Cl.
*A61K 38/51* (2006.01)
*A61K 47/60* (2017.01)
*A61K 45/06* (2006.01)
*C12N 9/88* (2006.01)
*A61K 31/223* (2006.01)

(52) U.S. Cl.
CPC .............. *A61K 38/51* (2013.01); *A61K 45/06* (2013.01); *A61K 47/60* (2017.08); *C12N 9/88* (2013.01); *A61K 31/223* (2013.01); *C12Y 404/01001* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,473,646 A | 9/1984 | Guy et al. |
| 5,091,308 A | 2/1992 | Klegerman et al. |
| 5,126,134 A | 6/1992 | Heim et al. |
| 5,382,657 A | 1/1995 | Karasiewicz et al. |
| 5,679,350 A | 10/1997 | Jankun et al. |
| 5,690,929 A | 11/1997 | Lishko et al. |
| 5,715,835 A | 2/1998 | Lishko et al. |
| 5,747,475 A | 5/1998 | Nordquist et al. |
| 5,759,542 A | 6/1998 | Gurewich |
| 5,766,897 A | 6/1998 | Braxton |
| 5,767,298 A | 6/1998 | Daleke |
| 5,888,506 A | 3/1999 | Tan |
| 5,972,885 A | 10/1999 | Spira et al. |
| 6,004,555 A | 12/1999 | Thorpe et al. |
| 6,051,230 A | 4/2000 | Thorpe et al. |
| 6,093,399 A | 7/2000 | Thorpe et al. |
| 6,132,729 A | 10/2000 | Thorpe et al. |
| 6,156,321 A | 12/2000 | Thorpe et al. |
| 6,165,509 A | 12/2000 | Hoffman et al. |
| 6,177,087 B1 | 1/2001 | Greenwald et al. |
| 6,217,869 B1 | 4/2001 | Meyer et al. |
| 6,231,854 B1 | 5/2001 | Yuying |
| 6,312,694 B1 | 11/2001 | Thorpe et al. |
| 6,319,702 B1 | 11/2001 | Smith et al. |
| 6,406,693 B1 | 6/2002 | Thorpe et al. |
| 6,451,312 B1 | 9/2002 | Thorpe |
| 6,491,894 B1 | 12/2002 | Ruoslahti et al. |
| 6,528,481 B1 | 3/2003 | Burg et al. |
| 6,576,239 B1 | 6/2003 | Ruoslahti et al. |
| 6,610,651 B1 | 8/2003 | Ruoslahti et al. |
| 6,749,853 B1 | 6/2004 | Thorpe et al. |
| 6,783,760 B1 | 8/2004 | Thorpe et al. |
| 6,818,213 B1 | 11/2004 | Thorpe et al. |
| 6,933,281 B2 | 8/2005 | Rouslahti et al. |
| 7,067,109 B1 | 6/2006 | Thorpe et al. |
| 7,504,397 B2 | 3/2009 | Hummersone et al. |

(Continued)

FOREIGN PATENT DOCUMENTS

WO          9517908       7/1995

OTHER PUBLICATIONS

Suradji, E.W., et al. 2011 Parasitology 138: 1852-1862. (Year: 2011).*
Eda, S., et al. 2002 Cell Physiol Biochem 12: 373-384. (Year: 2002).*
Burrows, J.N., et al. 2013 Malaria Journal 12:187 (20 pages). (Year: 2013).*

(Continued)

*Primary Examiner* — Marsha Tsay
(74) *Attorney, Agent, or Firm* — Dunlap Codding, P.C.

(57) ABSTRACT

A method, composition, and kit for treating a malarial infection in a subject by using an enzyme conjugate comprising a variant cystathione-gamma-lyase and a targeting ligand which binds to erythrocytes infected with *Plasmodium* pathogens. The variant cystathione-gamma-lyase has methioninase activity. Also disclosed is a method of treating *Plasmodium*-infected blood by exposing the infected blood with the enzyme conjugate.

13 Claims, 6 Drawing Sheets
(2 of 6 Drawing Sheet(s) Filed in Color)
Specification includes a Sequence Listing.

(56) References Cited

U.S. PATENT DOCUMENTS

| | | | |
|---|---|---|---|
| 7,652,033 | B2 | 1/2010 | Van Meir et al. |
| 8,143,228 | B2 | 3/2012 | Mabjeesh |
| 8,168,603 | B2 | 5/2012 | Jing et al. |
| 8,394,799 | B2 | 3/2013 | Lee et al. |
| 8,507,492 | B2 | 8/2013 | Perrin-Ninkovic et al. |
| 8,557,814 | B2 | 10/2013 | Castelhano et al. |
| 8,691,866 | B2 | 4/2014 | Iliopoulos et al. |
| 8,906,374 | B2 | 12/2014 | Kim et al. |
| 8,940,936 | B2 | 1/2015 | Lee et al. |
| 8,962,577 | B2 | 2/2015 | Hanes et al. |
| 8,986,701 | B2 | 3/2015 | Harrison |
| 9,040,574 | B2 | 5/2015 | Wang et al. |
| 9,062,072 | B2 | 6/2015 | Van Meir et al. |
| 9,987,241 | B2 | 6/2018 | Harrison, Jr. et al. |
| 2002/0150984 | A1 | 10/2002 | Mochly-Rosen et al. |
| 2003/0045496 | A1 | 3/2003 | Miki et al. |
| 2004/0170620 | A1 | 9/2004 | Thorpe et al. |
| 2006/0028584 | A1 | 11/2006 | Lind et al. |
| 2006/0275371 | A1 | 12/2006 | Dai et al. |
| 2011/0200576 | A1* | 8/2011 | Georgiou .......... A61P 35/00 424/94.5 |
| 2013/0323284 | A1 | 12/2013 | Alonso |
| 2014/0147432 | A1 | 5/2014 | Bancel et al. |
| 2015/0064159 | A1 | 3/2015 | Georgiou et al. |
| 2015/0064160 | A1 | 3/2015 | Georgiou et al. |
| 2016/0089350 | A1 | 3/2016 | Harrison, Jr. et al. |
| 2017/0044514 | A1 | 2/2017 | Georgiou et al. |

OTHER PUBLICATIONS

Mishra, S.K, et al. 2009 Current Opinion in Neurology 22: 302-307. (Year: 2009).*
Cobbold, S.A., et al. 2011 International Journal of Parasitology 41: 125-135. (Year: 2011).*
International Search Report, dated Oct. 19, 2018, in PCT/US2018/045968, filed Aug. 9, 2018.
Written Opinion of the International Searching Authority, dated Oct. 19, 2018, in PCT/US2018/045968, filed Aug. 9, 2018.
HSU; "Tissue Culture Methods and Applications," Kruse and Patterson, Eds, Academic Press, NY, (1973), pp. 764-767.
Halpern, B.C., et al.; "The Effect of Replacement of Methionine by Homocystine on Survival of Malignant and Normal Adult Mammalian Cells in Culture," Proc. Nat. Acad. Sci. USA; (1974), vol. 71, No. 4, pp. 1133-1136.
Embleton, et al.; "Monoclonal Antibodies to Osteogeni Sarcoma Antigens," Immunology Series; (1984); vol. 23, pp. 181-207.
Marquardt, H., et al.; "Rat Transforming Growth Factor Type I: Structure and Relation to Epidermal Growth Factor," Science, (1984), vol. 223, No. 4640, pp. 1079-1082.
Stoppelli, M.P., et al.; "Differentiation-Enhanced Binding of the Amino-Terminal Fragment of Human Urokinase Plasminogen Activator to a Specific Receptor on U937 Monocytes," Proc. Natl. Acad. Sci. USA; (1985), vol. 82, pp. 4939-4943.
Appella, E., et al.; "The Receptor-Binding Sequence of Urokinase," J. Biol. Chem.; (1987), vol. 262, No. 10, pp. 4437-4440.
Kimmel, et al.; "In Vitro Drug Sensitivity Testing in Human Gliomas," J. Neurosurg.; (1987), vol. 66, pp. 161-171.
Muraguchi, A., et al.; "The Essential Role of B Cell Stimulatory Factor 2 (BSF-2/IL-6) for the Terminal Differentiation of B Cells," J. Exp. Med.; (1988), vol. 167, pp. 332-344.
Argos, Patrick; "An Investigation of Oligopeptides Linking Domains in Protein Tertiary Structures and Possible Candidates for General Gene Fusion," J. Mol. Biol.; (1990), vol. 211, pp. 943-958; see figure 2, p. 950.
Chen, L., et al.; "IL-6 Receptors and Sensitivity to Growth Inhibition by IL-6 in Clones of Human Breast Carcinoma Cells," J. Biol. Regul. Homeost. Agents; (1991), vol. 5, No. 4, pp. 125-136.
Prior, T.I., et al.; "Cytotoxic Activity of a Recombinant Fusion Protein Between Insulin-Like Growth Factor I and Pseudomonas Exotoxin," Cancer Res.; (1991), vol. 51, pp. 174-180.

Utsugi, et al.; "Elevated Expression of Phosphatidylserine in the Outer Membrane Leaflet of Human Tumor Cells and Recognition by Activated Human Blood Monocytes," Cancer Res.; (1991), vol. 51, No. 11, pp. 3062-3066.
Boon, Thierry; "Toward a Genetic Analysis of Tumor Rejection Antigens,"; Ludwig Institute for Cancer Research; (1992), vol. 58, pp. 177-210.
Rao, et al.; "Binding of Annexin V to a Human Ovarian Carcinoma Cell Line" (OC-2008). Contrasting Effects on Cell Surface Factor VIIa/Tissue Factor Activity and Prothrombinase Activity, Thromb Res.; (1992), vol. 67, No. 5, pp. 517-531.
Pastan, I., et al.; "Recombinant Toxins as Novel Therapeutic Agents," Annu. Rev. Biochem.; (1992), vol. 61, pp. 331-354. Abstract only.
Drexler, Hans G.; "Recent Results on the Biology of Hodgkin and Reed-Sternberg Cells," Leukemia and Lymphoma; (1993), vol. 9, pp. 1-25.
Abbaszadegan, et al.; "Analysis of Multidrug Resistance-associated Protein (MRP) Messenger RNA in Normal and Malignant Hematopoietic Cells," Cancer Res.; (1994), vol. 54, pp. 4676-4679.
Dermer, Gerald D. "Another Anniversary for the War on Cancer," Bio/Technology; (1994), vol. 12, p. 320.
Phillips, et al.; "Transforming Growth Factor-α-Pseudomonas Exotoxin Fusion Protein (TGF-α-PE38) Treatment of Subcutaneous and Intracranial Human Glioma and Medulloblastoma Xenografts in Athymic Mice1," American Association for Cancer Research.; (1993), vol. 54, pp. 1008-1015.
Stanton, et al.; "Epidermal Growth Factor Receptor Expression by Human Squamous Cell Carcinomas of the Head and Neck, Cell Lines and Xenografts," Br. J. Cancer; (1994), vol. 70, pp. 427-433.
Kobayashi, et al.; "Inhibitory Effect of a Conjugate between Human Urokinase and Urinary Trypsin Inhibitor on Tumor Cell Invasion in Vitro," J. Biol. Chem.; (1995), vol. 270, No. 14, pp. 8361-8366.
Tait, et al.; "Prourokinase-Annexin V Chimeras, Construction, Expression, and Characterization of Recombinant Proteins," The Journal of Biological Chemistry; (1995), vol. 270, No. 37, pp. 21594-21599.
Tan, et al.; "Serum Methionine Depletion without Side Effects by Methioninase in Metastatic Breast Cancer Patients," Anticancer Research; (1996), vol. 16, pp. 3937-3942.
Kokkinakis, D.M., et al.; "Regulation of O6-methylguanine-DNA methyltransferase by methionine in human tumor Cells," British Journal of Cancer; (1997), vol. 75, pp. 779-788, Abstract only.
Tan, et al.; "Recombinant Methioninase Infusion Reduces the Biochemical Endpoint of Serum Methionine with Minimal Toxicity in High-Stage Cancer Patients," Anticancer Research; (1997), vol. 17, pp. 3857-3860.
Gooch, J.L., et al.; "Interleukin 4 Inhibits Growth and Induces Apoptosis in Human Breast Cancer Cells," American Association for Cancer Research; (1998), vol. 58, pp. 4199-4205.
Tan, et al.; "Polyethylene Glycol Conjugation of Recombinant Methioninase for Cancer Therapy," Protein Expression and Purification; (1998), vol. 12, pp. 45-52.
Iehlé, C., et al.; "Differences in steroid 5α-reductase iso-enzymes expression between normal and pathological human prostate tissue," J. Steroid Biochem. Mol. Biol.; (1999), vol. 68, pp. 189-195.
Bodey, et al.; "Failure of Cancer Vaccines: The Significant Limitations of this Approach to Immunotherapy," Anticancer Res.; (2000), vol. 20, pp. 2665-2676.
Kunkel, P., et al.; "Expression and Localization of Scatter Cactor/hepatocyte Growth Factor in Human Astrocytomas"; Neuro-Oncology; (2001), vol. 3, No. 2, pp. 82-88.
Taylor, et al.; "A Phase I and Pharmacodynamic Evaluation of Polyethylene Gloycol-Conjugated L-Asparaginase in Patients with Advanced Solid Tumors," Cancer Chemother. Pharmacol; (2001), vol. 47, pp. 83-88.
Ran, et al.; "Phosphatidylserine is a Marker of Tumor Vasculature and a Potential Target for Cancer Imaging and Therapy," Int. J. Radiation Oncology Biol. Phys.; (2002), vol. 54, No. 5, pp. 1479-1484.
Ran, et al.; "Increased Exposure of Anionic Phospholipids on the Surface of Tumor Blood Vessels," Cancer Res. (2002), vol. 62, pp. 6132-6140.

(56) References Cited

OTHER PUBLICATIONS

Yang, et al.; "Enhancing the Anticoagulant Potency of Soluble Tissue Factor Mutants by Increasing their Affinity to Factor VIIa," Thromb Haemost, (2002), vol. 87, pp. 450-458.
Zaslav, A.L., et al.; "Significance of a Prenatally Diagnosed del(10)(q23)," Amer. J. Medical Genetics; (2002), vol. 107, pp. 174-176.
Peron, et al.; "Targeting of a Novel Fusion Protein Containing Methioninase to the Urokinase Receptor to Inhibit Breast Cancer Cell Migration and Proliferation"; Cancer Chemother. Pharmacol.; (2003), vol. 52, pp. 270-276.
Van Dyke, D.L., et al.; "Monosomy 21 in Hematologic Diseases," Cancer Genetics and Cytogenetics; (2003), vol. 142, pp. 137-141.
Pento, et al.; "Influence of a Methioninase Containing Fusion Protein Targeted to the Urokinase Receptors on Breast Cancer Metastasis in Nude Mouse Xenografts," AACR Conference "Frontiers in Cancer Prevention Research," Seattle, WA; Oct. 2004.
Tian, J., et al.; "The Expression of Native and Cultured RPE Grown on Different Matrices," Physiol Genomics; (2001), vol. 17, pp. 170-182.
Zips, et al.; "New Anticancer Agents: In Vitro and In Vivo Evaluation," In Vivo; (2005), vol. 19, pp. 1-8.
Zang, et al.; "Internalizing Versus Non-internalizing Receptors for Targeting L-Methioninase to Cancer Cells," American Journal of Pharmacology and Toxicology; (2006), vol. 1, No. 3, pp. 60-64.
Kaiser, Jocelyn; "First Pass at Cancer Genome Reveals Complex Landscape," Science; (2006), vol. 313, p. 1370.
Mellman, Ira.; "Where Next for Cancer Immunotherapy," The Scientist; (2006), vol. 20, No. 1, pp. 177-210.
Kenis, et al.; "Annexin A5: Shifting From a Diagnostic Towards a Therapeutic Realm," Cell. Mol. Life Sci.; (2007), vol. 64, pp. 2859-2862.
Dumler, et al.; "Urokinase Activates the Jak/Stat Signal Trasduction Pathway in Human Vascular Endothelial Cells," Aarterioscler Thromb Vasc Biol (1999), vol. 19, pp. 290-297.
Jafferali, S., et al.; "Insulin-Like Growth Factor-I and Its Receptor in the Frontal Cortex, Hippocampus, and Cerebellum of Normal Human and Alzheimer Disease Brains," Synapse (2000), vol. 38, pp. 450-459.
Krais, et al.; "Antitumor Synergism and Enhanced Survival with a Tumor Vasculature—Targeted Enzyme Prodrug System, Rapamycin, and Cyclophosphamide," American Association for Cancer Research Molecular Cancer Therapeutics (2017), pp. 1-11.
Dutcher, Janice P.; "Mammalian Target of Rapamycin (mTOR) Inhibitors," Current Oncology Reports (2004), vol. 6, pp. 111-115.
Zaytseva, et al.; "mTOR Inhibitors in Cancer Therapy," Cancer Letters (2012), vol. 319, pp. 1-7.
Gerke, et al.; "Annexins: From Structure to Function," Physiol Rev (2002), vol. 82, pp. 331-371.
Azuma, et al.; "Development of Immunoadjuvants for Immunotherapy of Cancer," International Immunopharmacology (2001), vol. 1, pp. 1249-1259.
Deonarain, et al.; "Targeting Enzymes for Cancer Therapy: Old Enzymes in New Roles," Br J. Cancer (1994), vol. 70, pp. 786-794.
Dredge, et al.; "Adjuvants and the promotion of Th1-type Cytokines in Tumour Immunotherapy," Cancer Immunol Immunother (2002), vol. 51, pp. 521-531.
Hahn, et al.; "Thermochemotherapy: Synergism Between Hyperthermia (42-43°) and Adriamycin (or Bleomycin) in Mammalian Cell Inactivation," Proc. Nat. Acad. Sci. (1975), vol. 72, No. 3, pp. 937-940.
Hurwitz, et al.; "Combination Immunotherapy of Primary Prostate Cancer in a Transgenic Mouse Model Using CTLA-4 Blockade1," Cancer Research (2000), vol. 60, pp. 2444-2448.
Naylor, et al.; "In situ Photoimmunotherapy: a Tumour-directed Treatment for Melanoma," British Journal of Dermatology (2006), vol. 155, pp. 1287-1292.
Peng, et al.; "PD-1 Blockade Enhances T Cell Migration to Tumors by Elevating IFN-γ Inducible Chemokines," Cancer Research (2012), vol. 72, No. 20, pp. 5209-5218.
Stagg, et al.; Anti-CD73 Antibody Therapy Inhibits Breast Tumor Growth and Metastasis, PNAS (2010), vol. 107, No. 4, pp. 1547-1552.
Storm, FK; "Clinial Hyperthermia and Chemotherapy," Radiol Clin North Am. (1989), vol. 27, No. 3, pp. 621-627.
Van der Zee, J.; Heating the Patient: a Promising Approach?, Annals of Oncology (2002), vol. 13, pp. 1173-1184.
Weiss, et al.; "Immunotherapy of Cancer by IL-12-based Cytokine Combinations," Expert Opin Biol Ther. (2007), vol. 7, No. 11, pp. 1705-1721.
Melton, R., et al.; "Antibody-Enzyme Conjugates for Cancer Therapy," J. Natl Canc. Inst. (1996), vol. 88, No. 3/4, pp. 153-165; 1996.
Murata, T., et al.; "Two Different IL-13 Receptor Chains are Expressed in Normal Human Skin Fibroblasts, and IL-4 and IL-13 Mediate Signal Transduction Through a Common Pathway," Intl. Immun. (1998), vol. 10, No. 8, pp. 1103-1110.
Seigfried, S., et al.; "Distrinct Patterns of Expression of Keratinocyte Growth Factor and its Receptor in Endometrial Carcinoma," Cancer (1997), vol. 79, No. 6, pp. 1166-1171.
Vallera, D., et al.; "Targeting Urokinase-Type Plasminogen Activator Receptor on Human Glioblastoma Tumors With Diphtheria Toxin Fusion Protein DTAT," J. Natl Canc. Inst. (2002), vol. 94, No. 8, pp. 597-606.

\* cited by examiner

SEQUENCE LISTING

<160> NUMBER OF SEQ ID NOS: 4

<210> SEQ ID NO 1
<211> LENGTH: 398
<212> TYPE: PRT
<213> ORGANISM: Mus musculus

<400> SEQUENCE: 1

```
Met Gln Lys Asp Ala Ser Leu Ser Gly Phe Leu Pro Ser Phe Gln His
1               5                   10                  15

Phe Ala Thr Gln Ala Ile His Val Gly Gln Glu Pro Glu Gln Trp Asn
            20                  25                  30

Ser Arg Ala Val Val Leu Pro Ile Ser Leu Ala Thr Thr Phe Lys Gln
        35                  40                  45

Asp Phe Pro Gly Gln Ser Ser Gly Phe Glu Tyr Ser Arg Ser Gly Asn
    50                  55                  60

Pro Thr Arg Asn Cys Leu Glu Lys Ala Val Ala Ala Leu Asp Gly Ala
65                  70                  75                  80

Lys His Ser Leu Ala Phe Ala Ser Gly Leu Ala Ala Thr Ile Thr Ile
                85                  90                  95

Thr His Leu Leu Lys Ala Gly Asp Glu Ile Ile Cys Met Asp Glu Val
            100                 105                 110

Tyr Gly Gly Thr Asn Arg Tyr Phe Arg Arg Val Ala Ser Glu Phe Gly
        115                 120                 125

Leu Lys Ile Ser Phe Val Asp Cys Ser Lys Thr Lys Leu Leu Glu Ala
    130                 135                 140

Ala Ile Thr Pro Gln Thr Lys Leu Val Trp Ile Glu Thr Pro Thr Asn
145                 150                 155                 160

Pro Thr Leu Lys Leu Ala Asp Ile Gly Ala Cys Ala Gln Ile Val His
                165                 170                 175

Lys Arg Gly Asp Ile Ile Leu Val Val Asp Asn Thr Phe Met Ser Ala
            180                 185                 190

Tyr Phe Gln Arg Pro Leu Ala Leu Gly Ala Asp Ile Cys Met Cys Ser
        195                 200                 205

Ala Thr Lys Tyr Met Asn Gly His Ser Asp Val Val Met Gly Leu Val
    210                 215                 220

Ser Val Asn Ser Asp Asp Leu Asn Ser Arg Leu Arg Phe Leu Gln Asn
225                 230                 235                 240

Ser Leu Gly Ala Val Pro Ser Pro Phe Asp Cys Tyr Leu Cys Cys Arg
                245                 250                 255

Gly Leu Lys Thr Leu Gln Val Arg Met Glu Lys His Phe Lys Asn Gly
            260                 265                 270

Met Ala Val Ala Arg Phe Leu Glu Thr Asn Pro Arg Val Glu Lys Val
        275                 280                 285

Val Tyr Pro Gly Leu Pro Ser His Pro Gln His Glu Leu Ala Lys Arg
    290                 295                 300

Gln Cys Ser Gly Cys Pro Gly Met Val Ser Phe Tyr Ile Lys Gly Ala
305                 310                 315                 320

Leu Gln His Ala Lys Ala Phe Leu Lys Asn Leu Lys Leu Phe Thr Leu
                325                 330                 335

Ala Glu Ser Leu Gly Gly Tyr Glu Ser Leu Ala Glu Leu Pro Ala Ile
```

```
              340                 345                 350
Met Thr His Ala Ser Val Pro Glu Lys Asp Arg Ala Thr Leu Gly Ile
            355                 360                 365

Asn Asp Thr Leu Ile Arg Leu Ser Val Gly Leu Glu Asp Glu Gln Asp
        370                 375                 380

Leu Leu Glu Asp Leu Asp Arg Ala Leu Lys Ala Ala His Pro
385                 390                 395

<210> SEQ ID NO 2
<211> LENGTH: 405
<212> TYPE: PRT
<213> ORGANISM: Homo sapiens

<400> SEQUENCE: 2

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320
```

Thr Leu Gln His Ala Glu Ile Phe Leu Lys Asn Leu Lys Leu Phe Thr
                    325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 3
<211> LENGTH: 398
<212> TYPE: PRT
<213> ORGANISM: artificial sequence
<220> FEATURE:
<223> OTHER INFORMATION: variant of SEQ ID NO:1

<400> SEQUENCE: 3

Met Gln Lys Asp Ala Ser Leu Ser Gly Phe Leu Pro Ser Phe Gln His
1               5                   10                  15

Phe Ala Thr Gln Ala Ile His Val Gly Gln Glu Pro Glu Gln Trp Asn
            20                  25                  30

Ser Arg Ala Val Val Leu Pro Ile Ser Leu Ala Thr Thr Phe Lys Gln
        35                  40                  45

Asp Phe Pro Gly Gln Ser Ser Gly Phe Asn Tyr Ser Arg Ser Gly Asn
    50                  55                  60

Pro Thr Arg Asn Cys Leu Glu Lys Ala Val Ala Ala Leu Asp Gly Ala
65                  70                  75                  80

Lys His Ser Leu Ala Phe Ala Ser Gly Leu Ala Ala Thr Ile Thr Ile
                85                  90                  95

Thr His Leu Leu Lys Ala Gly Asp Glu Ile Ile Cys Met Asp Glu Val
            100                 105                 110

Tyr Gly Gly Thr Asn Leu Tyr Phe Arg Arg Val Ala Ser Glu Phe Gly
        115                 120                 125

Leu Lys Ile Ser Phe Val Asp Cys Ser Lys Thr Lys Leu Leu Glu Ala
    130                 135                 140

Ala Ile Thr Pro Gln Thr Lys Leu Val Trp Ile Glu Thr Pro Thr Asn
145                 150                 155                 160

Pro Thr Leu Lys Leu Ala Asp Ile Gly Ala Cys Ala Gln Ile Val His
                165                 170                 175

Lys Arg Gly Asp Ile Ile Leu Val Val Asp Asn Thr Phe Met Ser Ala
            180                 185                 190

Tyr Phe Gln Arg Pro Leu Ala Leu Gly Ala Asp Ile Cys Met Cys Ser
        195                 200                 205

Ala Thr Lys Tyr Met Asn Gly His Ser Asp Val Val Met Gly Leu Val
    210                 215                 220

Ser Val Asn Ser Asp Asp Leu Asn Ser Arg Leu Arg Phe Leu Gln Asn
225                 230                 235                 240

Ser Leu Gly Ala Val Pro Ser Pro Phe Asp Cys Tyr Leu Cys Cys Arg
                245                 250                 255

Gly Leu Lys Thr Leu Gln Val Arg Met Glu Lys His Phe Lys Asn Gly
            260                 265                 270

```
Met Ala Val Ala Arg Phe Leu Glu Thr Asn Pro Arg Val Glu Lys Val
            275                 280                 285

Val Tyr Pro Gly Leu Pro Ser His Pro Gln His Glu Leu Ala Lys Arg
        290                 295                 300

Gln Cys Ser Gly Cys Pro Gly Met Val Ser Phe Tyr Ile Lys Gly Ala
305                 310                 315                 320

Leu Gln His Ala Lys Ala Phe Leu Lys Asn Leu Lys Leu Phe Thr Leu
                325                 330                 335

Ala Val Ser Leu Gly Gly Tyr Glu Ser Leu Ala Glu Leu Pro Ala Ile
            340                 345                 350

Met Thr His Ala Ser Val Pro Glu Lys Asp Arg Ala Thr Leu Gly Ile
        355                 360                 365

Asn Asp Thr Leu Ile Arg Leu Ser Val Gly Leu Glu Asp Glu Gln Asp
    370                 375                 380

Leu Leu Glu Asp Leu Asp Arg Ala Leu Lys Ala Ala His Pro
385                 390                 395
```

<210> SEQ ID NO 4
<211> LENGTH: 405
<212> TYPE: PRT
<213> ORGANISM: artificial sequence
<220> FEATURE:
<223> OTHER INFORMATION: variant of SEQ ID NO:2

<400> SEQUENCE: 4

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Asn Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
            85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240
```

-continued

```
Asn Ser Leu Gly Ala Val Pro Ser Pro Ile Asp Cys Tyr Leu Cys Asn
            245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405
```

ANTIMALARIAL ENZYME CONJUGATES, KITS CONTAINING SAME, AND METHODS OF PRODUCING AND USING SAME

CROSS-REFERENCE TO RELATED APPLICATIONS/INCORPORATION BY REFERENCE STATEMENT

This application is a US National Stage Application under 35 USC § 371 of International Application No. PCT/US2018/045968, filed Aug. 9, 2018; which claims benefit under 35 U.S.C. 119(e) of U.S. Provisional Application Ser. No. 62/543,172, filed Aug. 9, 2017, the entirety of which is hereby expressly incorporated herein by reference.

STATEMENT REGARDING FEDERALLY SPONSORED RESEARCH OR DEVELOPMENT

Not Applicable.

BACKGROUND

Malaria is the single deadliest infectious disease. *Plasmodium* parasites may well be responsible for half of all human deaths, infecting 214 million individuals a year and killing a total of 438,000 people, most of whom are children. As recently as the year 2000, malaria claimed almost 1 million lives a year. This impressive decrease in malaria-associated mortality is in large part due to increased mosquito control and the cavalier use of antimalarial medicine.

Malaria is spread by the *Anopheles* mosquito. The vast majority of the world's population lives within the range of the *Anopheles* mosquito and is at risk of infection. Malaria is caused by an infection of the blood by protozoan parasites of the *Plasmodium* genus, which includes *P. vivax, P. ovale, P. malariae, P. knowlesi,* and *P. falciparum*. Of these parasites, *P. falciparum* is considered to be the most deadly. These strains are transmitted by the bite of mosquitos that have previously fed on infected victims. After entering the bloodstream, the *Plasmodium* parasites begin a complex multistage lifecycle characterized by both liver and blood infections. The blood stage is of prime clinical importance because it is the chief physiological cause of symptoms.

During the blood stage of infection, the parasite invades host erythrocytes (red blood cells). Once inside the host cell, the parasite rapidly grows, consuming the erythrocyte from the inside out. Replicating asexually, parasites quickly fill the infected red blood cell. The red blood cell then explodes, releasing numerous parasites into the bloodstream. During erythrocyte invasion and subsequent parasite growth, the parasites induce multiple physiological changes to its host. These changes are the direct result of hundreds of parasite-derived proteins being exported to the cell's surface. These proteins help transport necessary nutrients to the parasite and assist in immune evasion. Additionally, to fuel rapid growth, the parasite consumes much of the parasitized cell's inner contents.

The growth of the malaria parasite within its host red blood cell is characterized by several different stages. The free floating stage of the parasite, before it infects a red blood cell, is a merozoite. Immediately upon entering a host cell, the merozoite induces multiple changes in its structure, entering the ring stage. During the ring stage, the parasite begins to consume erythrocyte proteins, and as the parasite grows, it soon enters the trophozoite stage. In the trophozoite stage, the parasite induces multiple changes to the erythrocyte, creating multiple organelles and modifying its external membrane. In the final stage of parasite growth, the schizont stage, the parasite rapidly divides, producing multiple nuclei. This complex life cycle has contributed to the difficulty in developing a completely effective antimalarial treatment.

Current chemotherapeutics employed in the treatment of malaria include such drugs as chloroquine and artesunate. These drugs have been the mainstay of antimalarial therapy for several decades. However, widespread drug resistance has significantly reduced their efficacy in many regions. Common side effects of chloroquine include muscle problems, loss of appetite, diarrhea, and skin rash; serious side effects of chloroquine include problems with vision, muscle damage, seizures, and low blood cell levels. Side effects of artesunate may include a slow heartbeat, allergic reaction, dizziness, and low white blood cell levels.

Despite decreases in mortality from malaria, there has been an increase in the annual number of malaria cases. Compounding this issue is the pervasive rise of drug resistant strains of malaria. There is resistance to all major pharmaceutical treatments for malaria. High mortality, rising case numbers, and the spread of drug resistance has breathed a new sense of urgency into the search for novel antimalarial agents. The present disclosure provides one such novel antimalarial treatment.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

*dium* parasite *P. yoelii*. Pooled blood parasitemia was 4.0%. Erythrocytes were extracted from the blood and washed to remove debris. The blood was then incubated with varying concentrations of mCGL-AV for 3 hours. The blood was then washed to remove excess protein and debris. Samples were then incubated under an oxygen reduced atmosphere mimicking the conditions of blood within the body for 12 hours. The blood was then washed to remove excess protein and debris. The treated blood was stained with propidium iodide to reveal the presence of nonviable cells, and nonviable cells were enumerated via flow cytometry. The number of nonviable cells is expressed as a percentage of the total number of parasitized cells.

Figure 4:
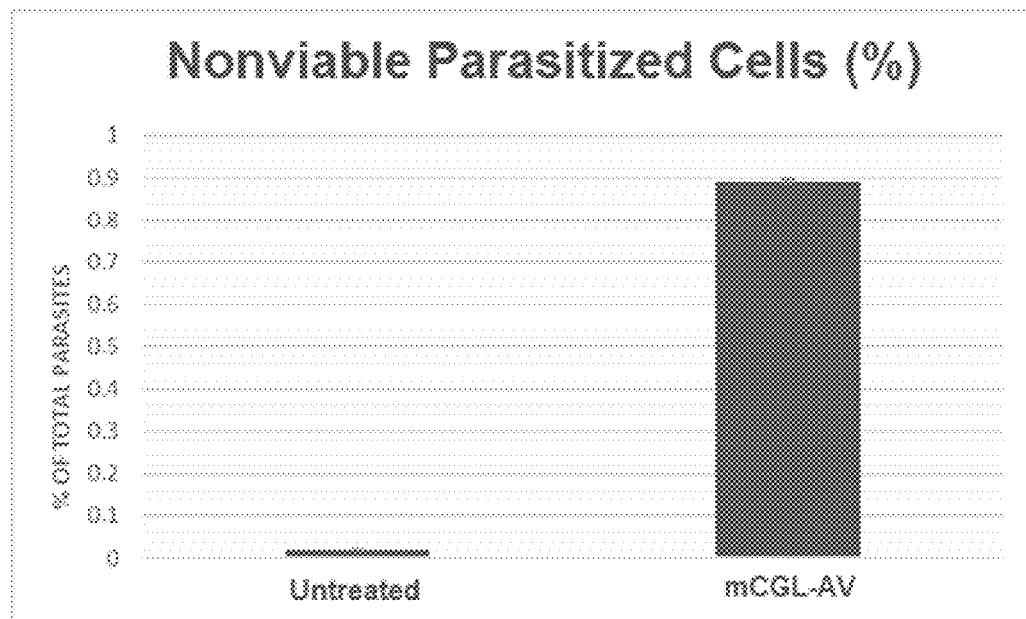

FIG. 4 shows that in hyperparasitized blood with 24% of all erythrocytes being infected with *Plasmodium* parasites, incubation with excess mCGL-AV (1.8 µM) resulted in almost complete killing of all infected cells within a short period. Blood was harvested and pooled from three mice infected with the murine *Plasmodium* parasite *P. yoelii*. Pooled blood parasitemia was 24.0%. Erythrocytes were extracted from the blood and washed to remove debris. The cells were then incubated with excess mCGL-AV for 3 hours. After incubation, the cells were then washed to remove excess protein and debris. The cells were stained with propidium iodide to reveal the presence of nonviable cells, and nonviable cells were enumerated via flow cytometry. The number of nonviable cells is expressed as a percentage of the total number of parasitized cells (with 1 equaling 100%, 0.9 equaling 90%, etc.). Error bars represent the standard error of n=3 repeats of the assay for the same pooled blood.

Figure 5:
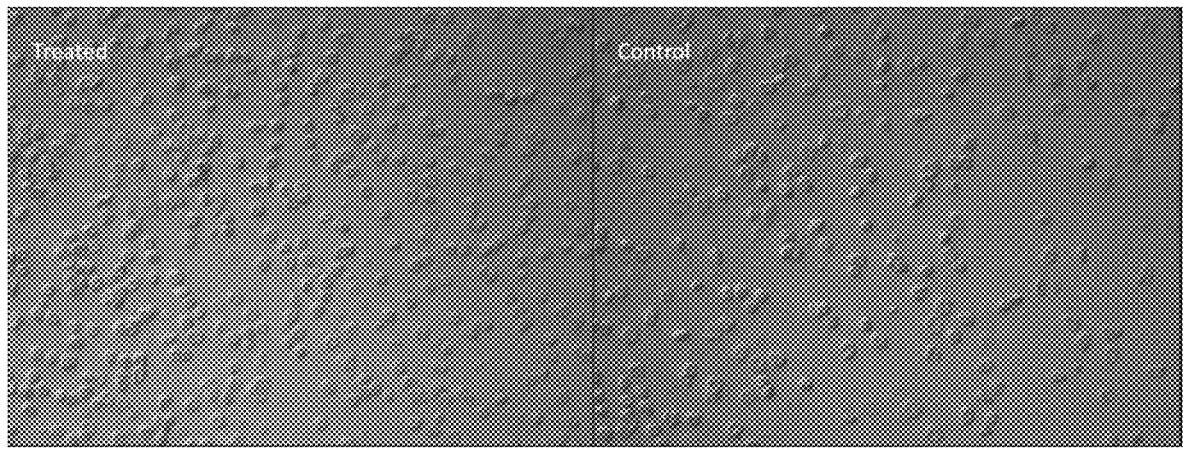

FIG. 5 shows micrographs demonstrating that mCGL-AV does not cause the lysis of intact red blood cells. There were no observable microscopic differences between blood treated with excess mCGL-AV (left) and a control untreated sample (right). Blood was harvested and pooled from three mice infected with the murine *Plasmodium* parasite *P. yoelii*. Pooled blood parasitemia was 24.0%. Erythrocytes were extracted from the blood and washed to remove debris. The cells were then incubated with excess mCGL-AV for 3 hours. After incubation, the cells were fixed in methanol. Fixed cells were stained with Giemsa stain and imaged with DIC light microscopy for the presence of hemolysis.

Figure 6:
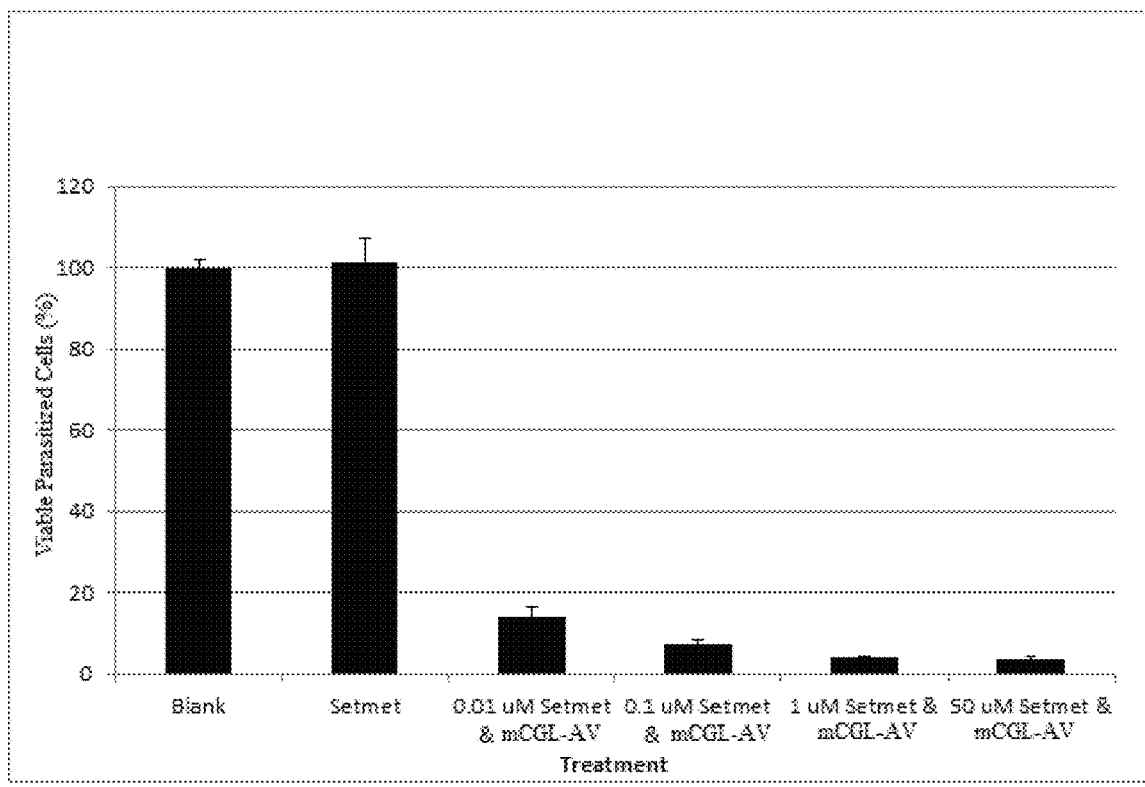

FIG. 6 shows that after 24 hours of culture, the mCGL-AV substrate selenomethionine (Setmet) had no significant impact on parasite viability by itself. However, parasites treated with both Setmet and mCGL-AV demonstrated a dose dependent relationship to varying concentrations of Setmet. Blood was harvested and pooled from three mice infected with the murine *Plasmodium* parasite *P. yoelii*. Pooled blood parasitemia was 4.0%. Erythrocytes were extracted from the blood and washed to remove debris. The cells were then incubated with excess mCGL-AV for 3 hours. After incubation, the cells were then washed to remove excess protein and debris. Samples were then incubated under an oxygen reduced atmosphere mimicking the conditions of blood within the body for 24 hours with varying concentrations of selenomethionine. Damaged parasites were enumerated via flow cytometry. The number of damaged parasites is expressed as a percentage of the total number of parasites. Error bars represent the standard error of n=3 repeats of the assay for the same pooled blood.

Figure 7:
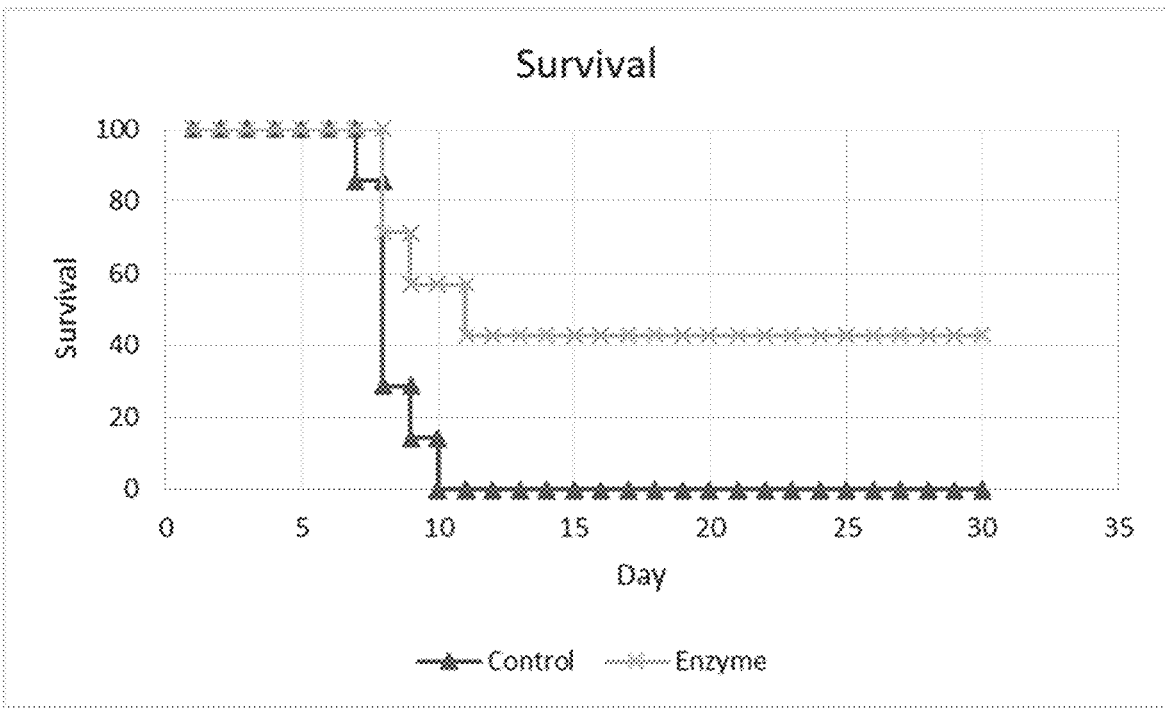

FIG. 7 shows survival of malarial mice treated with mCGL-AV (designated in the plot as "enzyme"). The mCGL-AV was assayed for antimalarial activity in a mouse model of malaria. In each group (n=7), 8 week old CF-1 mice were inoculated with the parasite *P. berghei*. The following day mice in the treated group received an i.p. injection of 10 mg/kg mCGL-AV. This single dose resulted in a significant increase in survival, and resulted in a complete cure in 3 of 7 mice treated with mCGL-AV. All untreated mice perished within 10 days. Surviving treated mice were euthanized for histology at day 30, and no parasites were detected at that time.

Figure 8:
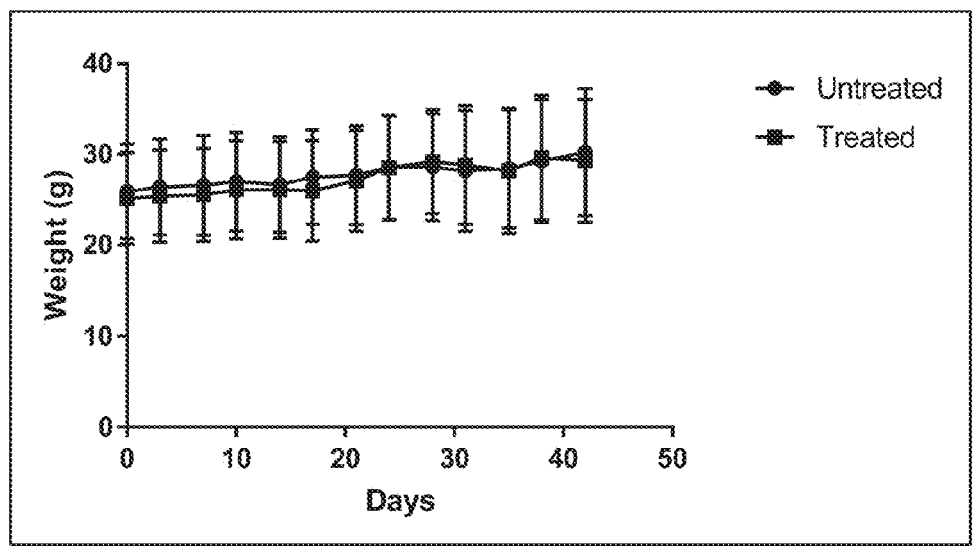

FIG. 8 shows that no drug related changes in mouse weight were observed with daily injections of the mCGL-AV fusion protein. The impact of mCGL-AV treatment on mouse health was assayed in part by monitoring mouse weight. Mice were treated daily with 10 mg/kg of mCGL-AV for a period of 20 days, and their weight was monitored for a period of one month.

Figure 9:
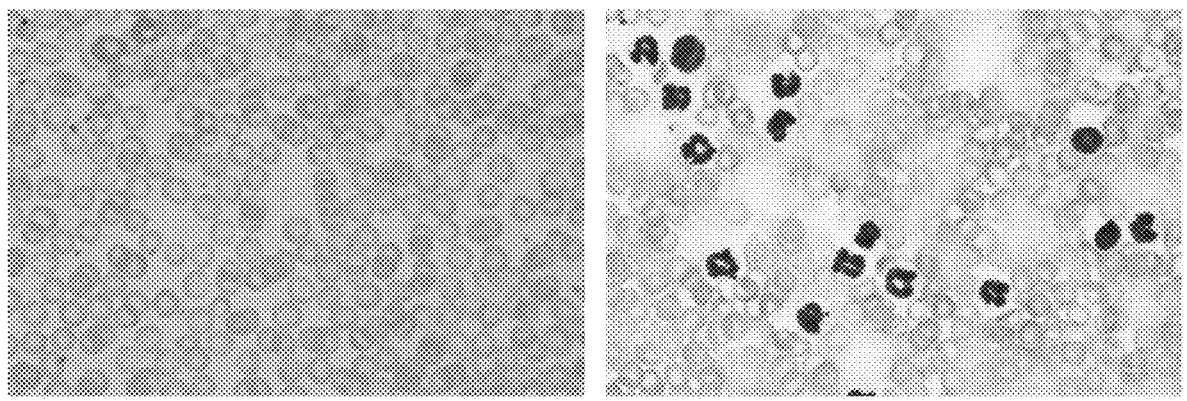

FIG. 9 contains micrographs of Giemsa-stained blood smears from mice inoculated with *P. berghei*. Mice treated with a single dose of 10 mg/kg of mCGL-AV 24 hours after parasite inoculation (left) demonstrated significant decreases in parasite burden compared to untreated controls (right). Parasites can be visualized as dark masses within infected erythrocytes in the untreated controls.

Figure 10:
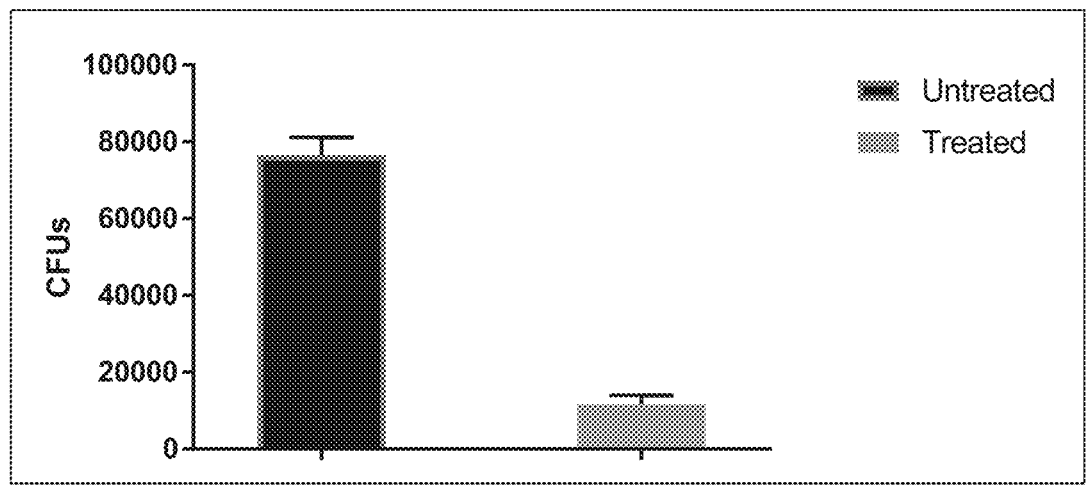

FIG. 10 shows quantitative results that mCGL-AV destroys intracellular bacteria. Mammalian cells were infected for 36 hours with intracellular *H. influenzae* bacteria and then treated with mCGL-AV. The number of viable bacteria (CFUs) was significantly reduced in cultures treated with the mCGL-AV.

Figure 11:
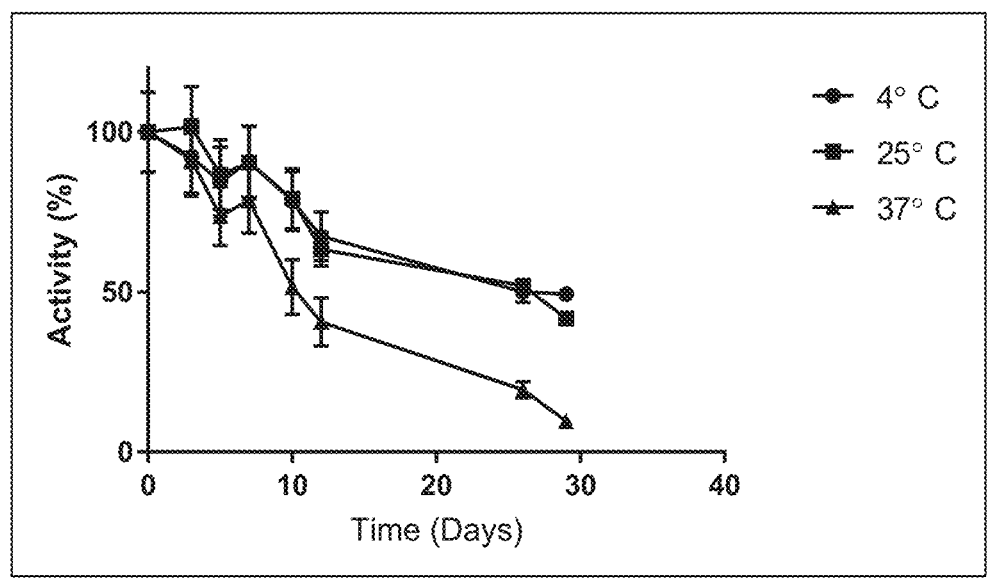

FIG. 11 shows that the mCGL-AV fusion protein retained significant activity for at least one month when stored at room temperature (25° C.) or refrigerated temperature (4° C.), particularly as compared to storage at 37° C.

DETAILED DESCRIPTION

The present disclosure is directed, in certain non-limiting embodiments, to methods of treating subjects infected with malarial parasites (*Plasmodium* sp.). The methods utilize a fusion protein (also referred to herein as an enzyme conjugate) comprising an enzyme having methioninase activity and a targeting ligand able to selectively bind to phosphatidylserine (PS) on surfaces of cells, particularly erythrocytes, which are infected by the malarial parasites. The method optionally includes co-administration of a prodrug which, when acted on by the enzyme of the fusion protein, forms a drug that is toxic to the infected cells. In at least one embodiment, the enzyme is a cystathione-γ-lyase (CGL) variant, and the targeting ligand is an annexin (such as, but not limited to, annexin V). Because the fusion protein is administered into the bloodstream, in addition to binding to erythrocytes, the fusion protein (enzyme conjugate) would penetrate into the liver and bind to parasite-infected liver cells having exposed phosphatidylserine. The present disclosure is further directed, in certain non-limiting embodiments, to a method for treating and/or purifying *Plasmodium*-infected blood by exposing the blood to the enzyme conjugate. The present disclosure is yet further directed, in certain non-limiting embodiments, to compositions and kits containing the enzyme conjugate, either alone or in combination with other compositions disclosed herein after.

Before providing further description of embodiments of the present disclosure by way of exemplary drawings, experimentation, results, and laboratory procedures, it is to be understood that the embodiments of the present disclosure are not limited in application to the details of compositions and methods set forth in the following description or illustrated in the drawings, experimentation, and/or results. The present disclosure is capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description only and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities, and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (4th ed., Cold Spring Harbor Laboratory Press, Cold Spring Harbor, N.Y. (2012) and Coligan et al. *Current Protocols in Immunology* (Current Protocols, Wiley Interscience (1991-2017)), which are incorporated herein by reference. The nomenclatures utilized in connection with, and the laboratory procedures and techniques of, analytical chemistry, synthetic organic chemistry, molecular and cellular biology, and medicinal and pharmaceutical chemistry described herein are those well known and commonly used in the art. Standard techniques are used for chemical syntheses, chemical analyses, pharmaceutical preparation, formulation and delivery, and treatment of patients.

All published patent applications, issued patents, and non-patent publications mentioned in the specification are indicative of the level of skill of those skilled in the art to which the presently disclosed inventive concepts pertain. All published patent applications, issued patents, and non-patent publications, including U.S. Pat. Nos. 8,709,407 and 9,987,241, are explicitly incorporated by reference herein to the same extent as if each individual published patent application, issued patent, or non-patent publication was specifically and individually indicated to be explicitly incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

Throughout this application, the term "about" is used to indicate that a value includes the inherent variation of error for the composition, the method used to administer the active agent or composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used in this specification, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. Further, all references to one or more embodiments or examples are to be construed as non-limiting to the claims.

As utilized in accordance with the present disclosure, the following terms, unless otherwise indicated shall be understood to have the following meanings:

As used herein, the terms "fusion protein" and "enzyme conjugate" may be used interchangeably. The term "mCGL" as used herein refers to a mutant cystathione-γ-lyase, as defined below. The term "methexin" as used herein refers to a mutant human cystathione-γ-lyase.

Where used herein, the terms "specifically binds to," "specific binding," "binds specifically to," and "binding specificity" refer to the ability of a ligand (e.g., an annexin) or other agent to detectably bind to a receptor or a binding epitope while having relatively little detectable reactivity with other proteins, epitopes, or receptor structures presented on cells to which the ligand or other agent may be exposed.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment," are DNA segments and smaller fragments of such segments, and also recombinant vectors, including, for example, plasmids, cosmids, phage, viruses, and the like. In this respect, the term "gene" is used for simplicity to refer to a functional protein-, polypeptide-, or peptide-encoding unit. As will be understood by those in the art, this functional term includes genomic sequences, cDNA sequences or combinations thereof. "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

In certain non-limiting embodiments, DNA sequences in accordance with the present disclosure may include genetic control regions which allow for the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of particular DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability to perform a desired biological activity in vitro or in vivo.

The DNA segments of the present disclosure encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to reduce antigenicity of the protein or to test mutants in order to examine biological activity at the molecular level or to produce mutants having changed or novel enzymatic activity and/or substrate specificity.

By "polypeptide" is meant a molecule comprising a series of amino acids linked through amide linkages along the alpha carbon backbone. Modifications of the peptide side chains may be present, along with glycosylations, hydroxylations, and the like. Additionally, other nonpeptide molecules, including lipids and small molecule agents, may be attached to the polypeptide.

Another embodiment of the present disclosure is a purified nucleic acid segment that encodes a protein or enzyme conjugate that functions in accordance with the present disclosure, further defined as being contained within a recombinant vector. As used herein, the term "recombinant vector" refers to a vector that has been modified to contain a nucleic acid segment that encodes a desired protein or fragment thereof. The recombinant vector may be further defined as an expression vector comprising a promoter operatively linked to said nucleic acid segment.

A further embodiment of the present disclosure is a host cell, made with a recombinant vector comprising one or more genes encoding one or more desired proteins, such as an enzyme conjugate. The recombinant host cell may be a prokaryotic cell. In another embodiment, the recombinant host cell is a eukaryotic cell. As used herein, the term "engineered" or "recombinant" cell is intended to refer to a cell into which one or more recombinant genes have been introduced mechanically or by the hand of man. Therefore, engineered cells are distinguishable from naturally occurring cells which do not contain a recombinantly-introduced gene. Engineered cells are thus cells having a gene or genes introduced therein through the hand of man. Recombinantly-introduced genes will either be in the form of a cDNA gene, a copy of a genomic gene, or will include genes positioned adjacent to a promoter associated, or not naturally associated, with the particular introduced gene.

In certain non-limiting embodiments, the DNA segments further include DNA sequences, known in the art functionally as origins of replication or "replicons," which allow replication of contiguous sequences by the particular host. Such origins allow the preparation of extrachromosomally localized and replicating chimeric or hybrid segments of plasmids, to which the desired DNA sequences are ligated. In certain instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The nucleic acid segments of the present disclosure, regardless of the length of the coding sequence itself, may be combined with other DNA sequences, such as (but not limited to) promoters, polyadenylation signals, additional restriction enzyme sites, multiple cloning sites, epitope tags, polyhistidine regions, other coding segments, and the like, such that their overall length may vary considerably. It is, therefore, contemplated that a nucleic acid fragment of almost any length may be employed, with the total length desirably being limited by the ease of preparation and use in the intended recombinant DNA protocol.

As used herein, an "enzyme conjugate" refers to a molecule that contains at least one receptor-binding ligand and at least one enzyme that are operably-linked. They may be coupled directly or via a linker and produced by chemical coupling methods or by recombinant expression of chimeric DNA molecules to produce fusion proteins.

As used herein, the terms "covalently coupled," "linked," "operably-linked," "bonded," "joined," and the like, with reference to the ligand and enzyme components of the enzyme conjugates of the present disclosure, mean that the specified components are either directly covalently bonded to one another or indirectly covalently bonded to one another through an intervening moiety or components, such as (but not limited to) a bridge, spacer, linker, or the like. Operably-linked moieties are associated in such a way so that the function of one moiety is not affected by the other, i.e., the moieties are connected in such an arrangement that they are configured so as to perform their usual function. The two moieties may be linked directly, or they may be linked indirectly via a linker sequence or molecule. For example but not by way of limitation, the ligand and the enzyme may be chemically coupled together via a thioether linkage. Another non-limiting example of a linkage is the covalent linking of the ligand and the enzyme by a flexible oligopeptide, e.g, as described by Argos ("An investigation of oligopeptides linking domains in protein tertiary structures and possible candidates for general gene fusion," *J. Mol. Biol.* (1990) 211:943-958).

The term "effective amount" refers to an amount of the enzyme conjugate (and optionally the prodrug and/or immunostimulant) sufficient to exhibit a detectable therapeutic effect when used in the manner of the present disclosure. The therapeutic effect may include, for example but not by way of limitation, reducing the concentration or numbers of *Plasmodium* parasites in a subject's blood, or reducing the number of infected erythrocytes in the subject's blood, or extending the survival of the subject, or ameliorating the symptoms of malaria in the subject. The effective amount for a subject will depend upon the type of subject, the subject's size and health, the nature and severity of the malarial condition to be treated, the method of administration, the duration of treatment, the nature of concurrent therapy (if any), the specific formulations employed, and the like. The effective amount for a given situation can be determined by one of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit, or control in the occurrence, frequency, severity, progression, or duration of the condition, e.g., malaria, or symptoms associated therewith, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition or disease, is also a successful treatment outcome. A therapeutic benefit therefore need not be complete ablation or reversal of the malarial infection, or any one, most, or all adverse symptoms, complications, consequences, or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

As used herein, the term "concurrent therapy" is used interchangeably with the terms "combination therapy" and "adjunct therapy," and will be understood to mean that the patient in need of treatment is treated or given another drug for the disease in conjunction with the enzyme conjugates of the present disclosure. This concurrent therapy can be sequential therapy, where the patient is treated first with one drug and then the other, or the two drugs can be administered simultaneously.

The term "pharmaceutically acceptable" refers to compounds and compositions which are suitable for administration to humans and/or animals without undue adverse side effects.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition). In certain non-limiting embodiments, a substantially purified fraction is a composition wherein the object species comprises at least about 50 percent (on a molar basis) of all macromolecular species present. In certain non-limiting embodiments, a substantially pure composition will comprise more than about 80 percent of all macromolecular species present in the composition, or more than about 85%, or more than about 90%, or more than about 95%, or more than about 99% of all macromolecular species present in the composition.

A "liposome" is a small vesicle composed of various types of lipids, phospholipids, and/or surfactants. The components of the liposome are commonly arranged in a bilayer formation, similar to the lipid arrangement of biological membranes.

The term "subject" is used interchangeably herein with the term "patient" and includes human and veterinary subjects, including any animal subject to a malarial parasitization. For purposes of treatment, the term "mammal" as used herein refers to any animal classified as a mammal, including (but not limited to) humans, non-human primates, monkeys, domestic animals (such as, but not limited to, dogs and cats), experimental mammals (such as mice, rats, rabbits, guinea pigs, and chinchillas), farm animals (such as, but not limited to, horses, pigs, cattle, goats, sheep, and llamas), and any other animal that has mammary tissue.

The terms "treat," "treating," and "treatment," as used herein, will be understood to include both inhibition of parasite growth as well as the killing of parasites and/or infected erythrocytes.

The term "receptor" as used herein will be understood to include any peptide, protein, glycoprotein, lipoprotein, polycarbohydrate, or lipid that is expressed or overexpressed on the surface of an a cell (such as (but not limited to) an erythrocyte that is infected by a *Plasmodium* species).

The phrase "substantially no internalization," as used herein, refers to a lack of internalization of a substantial amount of the enzyme conjugates of the present disclosure. For example, the phrase "substantially no internalization" will be understood as less than 25% of the enzyme conjugate bound to the cell surface being internalized by the cell, or less than 10% of the enzyme conjugate, or less than 5% of the enzyme conjugate, or less than 3% of the enzyme conjugate, or less than 1% of the enzyme conjugate being internalized by a cell to which the enzyme conjugate is bound.

The term "homologous" or "% identity" as used herein means a nucleic acid (or fragment thereof) or a peptide/protein (or a fragment thereof) having a degree of homology to the corresponding natural reference nucleic acid or peptide/protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (*Proc. Natl. Acad. Sci. USA* (1990) 87:2264-2268), modified as in Karlin & Altschul (*Proc. Natl. Acad. Sci. USA* (1993) 90:5873-5877).

In one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same.

Another example of a mathematical algorithm used for comparison of sequences is the algorithm of Myers & Miller (*CABIOS* (1988) 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (*Proc. Natl. Acad. Sci. USA* (1988) 85:2444-2448).

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish ("Local alignment statistics," Doolittle ed., *Methods in Enzymology* (1996) 266:460-480); Altschul et al. (*Journal of Molecular Biology* (1990) 215:403-410); Gish & States (*Nature Genetics* (1993) 3:266-272); Karlin & Altschul (*Proc. Natl. Acad. Sci. USA* (1993) 90:5873-5877); all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Specific amino acids may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

Turning now to the various embodiments of the present disclosure, certain non-limiting embodiments thereof are directed to enzyme conjugates (fusion proteins) that include an enzyme operatively attached to a ligand. The enzyme is able to convert a prodrug into an active antimalarial drug. The ligand has the ability to specifically and stably bind to an external receptor and/or binding site (such as, but not limited to, phosphatidylserine) on an outer surface of an infected cell, particularly (but not by way of limitation) an infected erythrocyte, and more particularly, an erythrocyte infected with a *Plasmodium* parasite. In at least one embodiment, the enzyme conjugate is maintained on the outer surface of an infected erythrocyte with substantially no internalization of the enzyme conjugate. In at least one embodiment, the external receptor and/or binding site is not present on an outer surface of an uninfected, healthy counterpart to the infected cell (i.e., an uninfected, healthy erythrocyte).

These enzyme conjugates may be utilized, for example (but not by way of limitation), in kits and in various methods of treating malaria, as described in detail herein below.

The enzyme conjugate may contain a variant (mutant) of the ligand. When a variant of the ligand is present in the enzyme conjugate, the only requirement is that the ligand variant substantially retains the ligand's receptor or targeting molecule binding activity. Also, sequences may be added to, or inserted within, the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions, deletions, and insertions to the native ligand's sequence that do not substantially affect the ligand's receptor binding activity. Such variations may occur at the nucleic acid level during construction of the construct from which the enzyme conjugate is expressed, or the variations may be produced by other posttranscriptional or posttranslational means known to those or ordinary skill in the art, including but not limited to, mutations and chemical modifications.

As stated above, the ligand portion of the enzyme conjugate specifically binds to the external receptor or binding site on the outer surface of the cell. In one non-limiting embodiment, the external receptor or binding site to which the conjugate binds is phosphatidylserine (PS). In this embodiment, the ligand may be selected from the group consisting of annexins or any ligand which specifically and stably binds to phosphatidylserine (PS), such as an antibody or other phosphatidylserine-binding protein.

Where used herein the term "annexin" refers to any of annexins 1-11 and 13, which are more particularly designated as annexins A1, A2, A3, A4, A5, A6, A7, A8, A9, A10, A11, and A13. Annexin I and annexin V where used herein refer to Annexin A1 and Annexin A5, respectively, for example. The annexins contemplated herein further include non-human cognate orthologs of A1-A11 and A13 from non-human vertebrates, including but not limited to non-human primates, dogs, cats, horses, livestock animals, and zoo animals, which may be used for treatment in said non-human mammals in the methods contemplated herein. The annexins contemplated for use herein are discussed in further detail in Gerke and Moss (*Physiol. Rev.* (2002) 82:331-371), the entirety of which is expressly incorporated by reference herein.

Anionic phospholipids are largely absent from the surfaces of resting mammalian cells under normal conditions. PS is the most abundant anionic phospholipid of the plasma membrane and is tightly segregated to the internal side of the plasma membrane in most cell types. Recently, it has been discovered that PS is expressed on the outside surface of red blood cells (erythrocytes) that are infected with malarial pathogens (e.g., *Plasmodium* sp.).

In one non-limiting embodiment of the enzyme conjugate of the present disclosure, human annexin V, a member of the annexin family of $Ca^{2+}$-dependent anionic phospholipid binding proteins (others are noted above), is used as the ligand and is operatively attached to or otherwise physically associated with the enzyme of the fusion protein. Annexin V is a member of a class of widely distributed annexin proteins which bind to anionic phospholipids and membranes in a $Ca^{2+}$-dependent manner. Annexin V is a monomeric protein which has been crystallized and shown to consist of four tandem repeats of similar structure. Structural evidence shows that the N-terminus of annexin V is located at the surface of the protein and faces away from the membrane-binding side of the molecule. It was later found that the attachment of prourokinase at the N-terminus of annexin V did not alter its affinity for cell membranes in which PS was exposed on the membrane surface, which is consistent with the previous structural evidence.

Annexin V (and other annexins) binds with very high affinity to PS-containing phospholipid bilayers. Annexin V may be obtained, for example, as described in U.S. Pat. No. 7,393,833, the entire contents of which are hereby expressly incorporated by reference. Endogenously administered annexin V actively localizes to PS expressing cells in vivo. The annexin portion of the fusion protein selectively binds to PS expressing cells. Annexin V, when conjugated to an active component, for example to form a fusion protein, can therefore be used to target PS-expressing cells, thereby localizing the fusion protein to the PS-expressing cells.

Examples of other PS-binding proteins that can be used in the fusion protein in substitution include (but are not limited to) those in the Annexin family (listed above), lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (including synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Alternatively, the ligand of the enzyme conjugate of the present disclosure may be an anionic phospholipid-specific antibody, such as (but not limited to) a PS-specific monoclonal antibody. Non-limiting examples of PS-specific monoclonal antibodies include those described in U.S. Pat. Nos. 6,312,694; 6,406,693; 6,783,760; 6,818,213; and 7,067,109.

The modification of one of the receptor-binding ligands described herein above to provide a fragment or variant thereof that substantially maintains the receptor binding ability of the native receptor-binding ligand is fully within the skill of a person in the art and therefore is also within the scope of the present disclosure. The term "substantially maintains the receptor-binding ability of the native receptor-binding ligand" means that the protein fragment or variant maintains at least about 50% of the native ligand's receptor-binding ability, at least about 75% of the native ligand's receptor-binding ability, at least about 90% of the native ligand's receptor-binding ability, or at least about 95% of the native ligand's receptor-binding ability.

In one non-limiting embodiment, the enzyme of the fusion protein may be L-methioninase (also known as methionine γ-lyase). In certain non-limiting embodiments, the enzyme is a non-L-methioninase that has methioninase activity (i.e., degrades the amino acid methionine), such as (but not limited to) a variant of a wild type mammalian cystathione-gamma-lyase (CGL). In at least one embodiment, the enzyme is a variant of wild type mouse CGL (SEQ ID NO:1, see Table 1) or of wild type human CGL (SEQ ID NO:2, see Table 2). A non-limiting example of one such variant is a variant of SEQ ID NO:1 (mouse CGL) having substitutions in positions 58 (e.g., E→N), 118 (e.g., R→L), and 338 (e.g., E→V) (SEQ ID NO:3). However, the particular amino acid substitutions listed above are for purposes of illustration only; any amino acid substitution at these positions in which methioninase activity is maintained is considered to be a suitable substitution. Other variants in mouse CGL may contain substitutions in only one or two of positions 58, 118, and 338. In one non-limiting variant, position 58 is substituted with valine rather than asparagine. Another non-limiting example of such a variant is a variant of SEQ ID NO:2 (human CGL) having substitutions in positions 59 (e.g., E→N), 119 (e.g., R→L), and 339 (e.g., E→V) (SEQ ID NO:4). However, the particular amino acid substitutions listed above are for purposes of illustration only; any amino acid substitution at these positions in which methioninase activity is maintained is considered to be a suitable substitution. Other variants in human CGL may contain substitutions in only one or two of positions 59, 119, and 339. For example, in another variant position 59 is substituted with valine rather than asparagine.

As noted above, the amino acids included in the substitutions in said CGL variants may include any amino acids other than those identified above which still enable the variant CGL to have methioninase activity. Possible substitutions include, but are not limited to, the conservative amino acid substitutions described in Table 3 below, and those identified in U.S. Pat. No. 8,709,407 (for example, in columns 2, 3, and 32 therein). Other variants include variants (with mutations in the homologous positions) of any other primate CGL (e.g., see U.S. Pat. No. 8,709,407, and Stone et al., "De Novo Engineering of a Human Cystathione-gamma-Lyase for Systemic L-Methionine Depletion Cancer Therapy," ACS Chem. Biol. (2012) 7:1822-1829), or other mammalian CGL, such as (but not limited to) dog, cat, and horse. Other variants include mutant CGLs which have additional substituted amino acids such that they have at least about 80% identity to the CGL sequences listed above, or at least about 81% identity thereto, or at least about 82% identity thereto, or at least about 83% identity thereto, or at least about 84% identity thereto, or at least about 85% identity thereto, or at least about 86% identity thereto, or at least about 87% identity thereto, or at least about 88% identity thereto, or at least about 89% identity thereto, or at least about 90% identity thereto, or at least about 91% identity thereto, or at least about 92% identity thereto, or at least about 93% identity thereto, or at least about 94% identity thereto, or at least about 95% identity thereto, or at least about 96% identity thereto, or at least about 97% identity thereto, or at least about 98% identity thereto, or at least about 99% identity thereto, wherein "% identity" is defined in at least one embodiment as the percentage of amino acids (or nucleotides) which are identical at corresponding positions in two amino acid (or nucleic acid) sequences of a protein (or nucleic acid). Said variants of CGL described herein have L-methioninase activity.

TABLE 1

Murine Cystathione-γ-Lyase (SEQ ID NO: 1)

| | | | | | | | | | | | | | | | |
|---|---|---|---|---|---|---|---|---|---|---|---|---|---|---|---|
| Met | Gln | Lys | Asp | Ala | Ser | Leu | Ser | Gly | Phe | Leu | Pro | Ser | Phe | Gln | His | (16) |
| Phe | Ala | Thr | Gln | Ala | Ile | His | Val | Gly | Gln | Glu | Pro | Glu | Gln | Trp | Asn | (32) |
| Ser | Arg | Ala | Val | Val | Leu | Pro | Ile | Ser | Leu | Ala | Thr | Thr | Phe | Lys | Gln | (48) |
| Asp | Phe | Pro | Gly | Gln | Ser | Ser | Gly | Phe | Glu | Tyr | Ser | Arg | Ser | Gly | Asn | (64) |
| Pro | Thr | Arg | Asn | Cys | Leu | Glu | Lys | Ala | Val | Ala | Ala | Leu | Asp | Gly | Ala | (80) |
| Lys | His | Ser | Leu | Ala | Phe | Ala | Ser | Gly | Leu | Ala | Ala | Thr | Ile | Thr | Ile | (96) |
| Thr | His | Leu | Leu | Lys | Ala | Gly | Asp | Glu | Ile | Ile | Cys | Met | Asp | Glu | Val | (112) |
| Tyr | Gly | Gly | Thr | Asn | Arg | Tyr | Phe | Arg | Arg | Val | Ala | Ser | Glu | Phe | Gly | (128) |
| Leu | Lys | Ile | Ser | Phe | Val | Asp | Cys | Ser | Lys | Thr | Lys | Leu | Leu | Glu | Ala | (144) |
| Ala | Ile | Thr | Pro | Gln | Thr | Lys | Leu | Val | Trp | Ile | Glu | Thr | Pro | Thr | Asn | (160) |
| Pro | Thr | Leu | Lys | Leu | Ala | Asp | Ile | Gly | Ala | Cys | Ala | Gln | Ile | Val | His | (176) |
| Lys | Arg | Gly | Asp | Ile | Ile | Leu | Val | Val | Asp | Asn | Thr | Phe | Met | Ser | Ala | (192) |
| Tyr | Phe | Gln | Arg | Pro | Leu | Ala | Leu | Gly | Ala | Asp | Ile | Cys | Met | Cys | Ser | (208) |
| Ala | Thr | Lys | Tyr | Met | Asn | Gly | His | Ser | Asp | Val | Val | Met | Gly | Leu | Val | (224) |
| Ser | Val | Asn | Ser | Asp | Asp | Leu | Asn | Ser | Arg | Leu | Arg | Phe | Leu | Gln | Asn | (240) |

TABLE 1-continued

Murine Cystathione-γ-Lyase (SEQ ID NO: 1)

| | | | | | | | | | | | | | | | |
|---|---|---|---|---|---|---|---|---|---|---|---|---|---|---|---|
| Ser | Leu | Gly | Ala | Val | Pro | Ser | Pro | Phe | Asp | Cys | Tyr | Leu | Cys | Cys | Arg | (256) |
| Gly | Leu | Lys | Thr | Leu | Gln | Val | Arg | Met | Glu | Lys | His | Phe | Lys | Asn | Gly | (272) |
| Met | Ala | Val | Ala | Arg | Phe | Leu | Glu | Thr | Asn | Pro | Arg | Val | Glu | Lys | Val | (288) |
| Val | Tyr | Pro | Gly | Leu | Pro | Ser | His | Pro | Gln | His | Glu | Leu | Ala | Lys | Arg | (304) |
| Gln | Cys | Ser | Gly | Cys | Pro | Gly | Met | Val | Ser | Phe | Tyr | Ile | Lys | Gly | Ala | (320) |
| Leu | Gln | His | Ala | Lys | Ala | Phe | Leu | Lys | Asn | Leu | Lys | Leu | Phe | Thr | Leu | (336) |
| Ala | Glu | Ser | Leu | Gly | Gly | Tyr | Glu | Ser | Leu | Ala | Glu | Leu | Pro | Ala | Ile | (352) |
| Met | Thr | His | Ala | Ser | Val | Pro | Glu | Lys | Asp | Arg | Ala | Thr | Leu | Gly | Ile | (368) |
| Asn | Asp | Thr | Leu | Ile | Arg | Leu | Ser | Val | Gly | Leu | Glu | Asp | Glu | Gln | Asp | (384) |
| Leu | Leu | Glu | Asp | Leu | Asp | Arg | Ala | Leu | Lys | Ala | Ala | His | Pro | | | (398) |

TABLE 2

Human Cystathione-γ-Lyase (SEQ ID NO: 2)

| | | | | | | | | | | | | | | | |
|---|---|---|---|---|---|---|---|---|---|---|---|---|---|---|---|
| Met | Gln | Glu | Lys | Asp | Ala | Ser | Ser | Gln | Gly | Phe | Leu | Pro | His | Phe | Gln | (16) |
| His | Phe | Ala | Thr | Gln | Ala | Ile | His | Val | Gly | Gln | Asp | Pro | Glu | Gln | Trp | (32) |
| Thr | Ser | Arg | Ala | Val | Val | Pro | Pro | Ile | Ser | Leu | Ser | Thr | Thr | Phe | Lys | (48) |
| Gln | Gly | Ala | Pro | Gly | Gln | His | Ser | Gly | Phe | Glu | Tyr | Ser | Arg | Ser | Gly | (64) |
| Asn | Pro | Thr | Arg | Asn | Cys | Leu | Glu | Lys | Ala | Val | Ala | Ala | Leu | Asp | Gly | (80) |
| Ala | Lys | Tyr | Cys | Leu | Ala | Phe | Ala | Ser | Gly | Leu | Ala | Ala | Thr | Val | Thr | (96) |
| Ile | Thr | His | Leu | Leu | Lys | Ala | Gly | Asp | Gln | Ile | Ile | Cys | Met | Asp | Asp | (112) |
| Val | Tyr | Gly | Gly | Thr | Asn | Arg | Tyr | Phe | Arg | Gln | Val | Ala | Ser | Glu | Phe | (128) |
| Gly | Leu | Lys | Ile | Ser | Phe | Val | Asp | Cys | Ser | Lys | Ile | Lys | Leu | Leu | Glu | (144) |
| Ala | Ala | Ile | Thr | Pro | Glu | Thr | Lys | Leu | Val | Trp | Ile | Glu | Thr | Pro | Thr | (160) |
| Asn | Pro | Thr | Gln | Lys | Val | Ile | Asp | Ile | Glu | Gly | Cys | Ala | His | Ile | Val | (176) |
| His | Lys | His | Gly | Asp | Ile | Ile | Leu | Val | Val | Asp | Asn | Thr | Phe | Met | Ser | (192) |
| Pro | Tyr | Phe | Gln | Arg | Pro | Leu | Ala | Leu | Gly | Ala | Asp | Ile | Ser | Met | Tyr | (208) |
| Ser | Ala | Thr | Lys | Tyr | Met | Asn | Gly | His | Ser | Asp | Val | Val | Met | Gly | Leu | (224) |
| Val | Ser | Val | Asn | Cys | Glu | Ser | Leu | His | Asn | Arg | Leu | Arg | Phe | Leu | Gln | (240) |
| Asn | Ser | Leu | Gly | Ala | Val | Pro | Ser | Pro | Ile | Asp | Cys | Tyr | Leu | Cys | Asn | (256) |
| Arg | Gly | Leu | Lys | Thr | Leu | His | Val | Arg | Met | Glu | Lys | His | Phe | Lys | Asn | (272) |
| Gly | Met | Ala | Val | Ala | Gln | Phe | Leu | Glu | Ser | Asn | Pro | Trp | Val | Glu | Lys | (288) |
| Val | Ile | Tyr | Pro | Gly | Leu | Pro | Ser | His | Pro | Gln | His | Glu | Leu | Val | Lys | (304) |
| Arg | Gln | Cys | Thr | Gly | Cys | Thr | Gly | Met | Val | Thr | Phe | Tyr | Ile | Lys | Gly | (320) |
| Thr | Leu | Gln | His | Ala | Glu | Ile | Phe | Leu | Lys | Asn | Leu | Lys | Leu | Phe | Thr | (336) |
| Leu | Ala | Glu | Ser | Leu | Gly | Gly | Phe | Glu | Ser | Leu | Ala | Glu | Leu | Pro | Ala | (352) |
| Ile | Met | Thr | His | Ala | Ser | Val | Leu | Lys | Asn | Asp | Arg | Asp | Val | Leu | Gly | (368) |

TABLE 2-continued

Human Cystathione-γ-Lyase (SEQ ID NO: 2)

Ile Ser Asp Thr Leu Ile Arg Leu Ser Val Gly Leu Glu Asp Glu Glu  (384)

Asp Leu Leu Glu Asp Leu Asp Gln Ala Leu Lys Ala Ala His Pro Pro  (400)

Ser Gly Ser His Ser  (405)

TABLE 3

Conservative and Semi-conservative Substitutions in Amino Acids

| Amino Acid Group | Conservative and Semi-Conservative Substitutions |
| --- | --- |
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

In a particular (but non-limiting) embodiment, the variant CGL enzyme of the enzyme conjugate is at least about 90% identical to a wild type CGL enzyme. In another particular (but non-limiting) embodiment, the variant CGL enzyme of the enzyme conjugate has an amino acid sequence that is at least about 90% identical to the amino acid sequence of SEQ ID NO:2 and has substitutions in positions 59, 119, and 339 thereof; and/or the variant CGL enzyme of the enzyme conjugate has an amino acid sequence that is at least about 90% identical to the amino acid sequence of SEQ ID NO:1 and has substitutions in positions 58, 118, and 338 thereof. In yet another particular (but non-limiting) embodiment, the variant CGL enzyme of the enzyme conjugate comprises an amino acid sequence of SEQ ID NO:3 or SEQ ID NO:4.

The proteins and fusion proteins of the present disclosure may be produced using any nucleotide sequence which encodes the desired amino acid sequence. The proteins may include, for example (but not by way of limitation), conservative substitutions of the amino acid residues of the CGL sequence described herein, wherein such amino acid substitutions do not substantially reduce the L-methioninase activities of the encoded enzyme variant. Examples of conservative amino acid substitutions include, but are not limited to, glycine:alanine substitutions; valine:isoleucine: leucine substitutions; asparagine:glutamine:histidine substitutions; aspartic acid:glutamic acid substitutions; serine: threonine:methionine substitutions; lysine:arginine:histidine substitutions; and phenylalanine:tyrosine:tryptophan substitutions. As noted, other examples of conservative and semi-conservative amino acid substitutions that may be utilized in accordance with the present disclosure are shown in Table 3. Other types of substitutions, variations, additions, deletions, and derivatives that result in functional CGL variants are also encompassed by the present disclosure, and one of ordinary skill in the art would readily know how to make, identify, or select such variants or derivatives, as well as how to test for methioninase activity of those variants.

The enzyme and the ligand of the enzyme conjugate may be directly coupled together (e.g., via a covalent bond) or indirectly coupled together via a linker, such as (but not limited to) via a linker peptide.

In one non-limiting embodiment, the enzyme conjugate includes (1) a cystathione-gamma-lyase (CGL) having methioninase activity, and (2) a targeting ligand specific to phosphatidylserine, such as (but not limited to) an annexin (e.g., one of annexins 1-13) or a functional variant thereof.

In alternate non-limiting embodiments, the enzyme conjugate includes (1) an amino acid sequence as set forth in SEQ ID NO:1 or 2, and (2) a targeting ligand specific to phosphatidylserine, such as (but not limited to) an annexin (e.g., one of annexins 1-13) or functional variants thereof.

In alternate non-limiting embodiments, the enzyme conjugate includes (1) a variant (mutant) of an amino acid sequence as set forth in SEQ ID NO:1 or 2 which has methioninase activity, and (2) a targeting ligand specific to phosphatidylserine, such as (but not limited to) an annexin (e.g., one of annexins 1-13) or a functional variant thereof.

In alternate non-limiting embodiments, the enzyme conjugate includes (1) a variant (mutant) of an amino acid sequence as set forth in SEQ ID NO:1 or 2 which has methioninase activity and is at least about 90% identical to SEQ ID NO:1 and/or 2, and (2) a targeting ligand specific to phosphatidylserine, such as (but not limited to) an annexin (e.g., one of annexins 1-13) or a functional variant thereof. In a particular non-limiting embodiment, the variant of (1) has an amino acid sequence that is at least about 90% identical to the amino acid sequence of SEQ ID NO:2 and has substitutions in positions 59, 119, and 339 thereof; and/or the variant of (1) has an amino acid sequence that is at least about 90% identical to the amino acid sequence of SEQ ID NO:1 and has substitutions in positions 58, 118, and 338 thereof.

The present disclosure is not to be regarded as being solely limited to the specific sequences disclosed herein. As described herein above, the scope of sequences contemplated herein may contain one or more substitutions, variations, additions, and deletions when compared to the specific sequences disclosed herein. For example, standardized and accepted functionally equivalent amino acid substitutions are presented in Table 3. One of ordinary skill in the art, given the present specification, would be able to identify, isolate, create, and test DNA sequences and/or enzymes that produce natural, mutant, chimeric, or hybrid molecules having the desired methioninase activity and/or specific targeting ability. As such, the present disclosure should not be regarded as being limited to the specific sequences disclosed herein.

A fusion protein comprising a variant mouse CGL with substitutions in positions 58, 118, and 338 of SEQ ID NO:1 was previously shown to not produce a detectable immune response in mice when it was injected daily for 21 consecutive days at a dose of 10 mg/kg per injection by i.p. injection (Krais, et al., "Antitumor Synergism and Enhanced Survival in Immune-Competent Mice Treated with a Vascular-Targeted Enzyme Prodrug System, Rapamycin, and Cyclophosphamide," *Molecular Cancer Therapeutics* (2017) 16:1855-65).

Enzymes of the enzyme conjugate of the present disclosure may be modified so as to reduce the immunogenicity thereof. One method for reducing a protein's immunogenicity is to conjugate the protein to polyethylene glycol (PEG). By "polyethylene glycol" or "PEG" is also meant any other polyalkylene glycol compound or a derivative thereof, with or without coupling agents or derivatization with coupling or activating moieties (e.g., with thiol, triflate, tresylate, azirdine, oxirane, or particularly with a maleimide moiety). Compounds such as maleimido monomethoxy PEG are exemplary of activated PEG compounds of the present disclosure. Other polyalkylene glycol compounds, such as (but not limited to) polypropylene glycol, may be used in accordance with the present disclosure. Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The PEG can be linked to any N-terminal amino acid of the enzyme conjugate, and/or can be linked to an amino acid residue downstream of the N-terminal amino acid, such as lysine, histidine, tryptophan, aspartic acid, glutamic acid, and cysteine, for example or other such linkable amino acids known to those of ordinary skill in the art. Cysteine-PEGylated enzyme conjugates, for example, are created by attaching polyethylene glycol to a thio group on a cysteine residue of the enzyme conjugate.

The PEG moiety attached to the enzyme conjugate may range in molecular weight, for example, but not limited to, from about 200 to about 40,000 MW.

The enzyme conjugates contemplated herein can be adsorbed or linked to PEG molecules using techniques shown, for example (but not limited to), in U.S. Pat. Nos. 4,179,337; 5,382,657; 5,972,885; 6,177,087; 6,165,509; 5,766,897; and 6,217,869; and Published Application 2006/0275371; the specifications and drawings each of which are hereby expressly incorporated by reference herein in their entirety.

The immunological response to the enzyme can be reduced or eliminated by either conjugation to PEG or by encapsulation in liposomes, without significant effect on enzymatic activity of the enzyme. Liposome encapsulation has the advantage that covalent attachment of moieties to the enzyme is not required, which may be helpful to preserve binding of the proposed enzyme conjugates to the receptors on infected cells. Thus, in certain non-limiting embodiments, the enzyme of the enzyme conjugate may be conjugated to polyethylene glycol (PEG), or may be encapsulated in a liposome.

Certain non-limiting embodiments of the present disclosure also include a purified nucleic acid segment encoding any of the enzyme-ligand conjugates described or otherwise contemplated herein, a recombinant vector comprising said nucleic acid segment, and a recombinant host cell comprising said recombinant vector.

In certain non-limiting embodiments, the enzyme conjugates described herein are utilized in combination with a prodrug which may be administered with the enzyme conjugate or separately from the enzyme conjugate. The prodrug utilized in accordance with the present disclosure is a substrate for the enzyme of the enzyme conjugate and therefore is convertible into an active drug by the enzyme of the enzyme conjugate. For example but not by way of limitation, a selenomethionine prodrug is converted to methylselenol by L-methioninase or a CGL having L-methioninase activity. In one non-limiting embodiment, the prodrug is converted to an active form by the enzyme of the enzyme conjugate at the site to which the enzyme conjugate is bound (such as (but not limited to) at the infected erythrocyte).

Certain non-limiting embodiments of the present disclosure include methods of treating a malarial infection in a subject. Practice of the methods may comprise administering to a subject in need of such treatment a therapeutically effective amount of any of the enzyme conjugates disclosed or otherwise contemplated herein, and optionally administering an effective amount of a prodrug, in any suitable systemic and/or local formulation and in therapeutically-effective amount(s). Non-limiting examples of therapeutically-effective amounts include amounts in a range of about 0.1 µg/kg to about 100 mg/kg of the enzyme conjugates and a range of about 0.1 µg/kg to about 100 mg/kg of the prodrug (when utilized). Typically, but not by way of limitation, one or more of the various compounds may be administered over multiple times (for example but not by way of limitation, from one to five times per day, or once or twice per week or month), or continuously or intermittently via a venous drip, depending on the desired therapeutic effect. In one non-limiting example of a therapeutic method of the present disclosure, one or more of the compounds are provided in an IV infusion in a range of from about 1 mg/kg to about 10 mg/kg of body weight once a day. In addition, when multiple compositions are administered as part of the method, the compositions may be administered simultaneously or wholly or partially sequentially.

In a particular (but non-limiting) embodiment, the enzyme conjugate comprises a ligand bound to a variant cystathione-gamma-lyase having L-methioninase activity. The binding of the enzyme conjugate to the surface of an infected cell (such as, but not limited to, an infected red blood cell) results in a depletion of methionine ("methionine starvation") in a vicinity of the infected cell, whereby the enzyme conjugate itself is also selectively toxic to the cell and the parasites within the cell.

When the method includes the additional step of administering the prodrug to the subject, in a particular (but non-limiting) embodiment, the enzyme conjugate and prodrug are administered sequentially. In this non-limiting embodiment, the method may further include the step of allowing unbound enzyme conjugate to be substantially cleared from the bloodstream of the subject before administering the prodrug.

In another non-limiting embodiment, the enzyme conjugate compositions and methods of use thereof are combined with the use of an immunostimulant. The destruction of the erythrocyte cells causes pathogenic antigens to be released into the bloodstream. The antigens alone may not be sufficient to stimulate an appropriate immune response. However, the addition of an immunostimulant helps the immune system to mount a systemic attack on antigens derived from the pathogenic organisms.

Any immunostimulant known in the art or otherwise capable of functioning in accordance with the present disclosure may be utilized in the compositions, kits, and methods described herein. Examples of immunostimulants that may be utilized in accordance with the present disclosure include, but are not limited to, cyclophosphamide, glycated chitosan (Naylor et al. (2006) *The British Journal of Dermatology*, 155:1287-1292); muramyldipeptide derivatives; trehalose-dimycolates; and BCG-cell wall skeleton (Azuma et al. (2001) *International Immunopharmacology*, 1:1249-1259); various cytokines (Weiss et al. (2007) *Expert opinion on biological therapy*, 7:1705-1721); anti-CTLA-4 monoclonal antibody (Hurwitz et al. (2000) *Cancer Research*, 60:2444-2448); anti-PD-1 monoclonal antibody (Peng et al. (2012) *Cancer Research*, 72:5209-5218); anti-CD73 monoclonal antibody (Stagg et al. (2010) *Proc. Nt. Acad. Sci.*, 107:1547-1522); and combinations and/or derivatives thereof. Any dosage of immunostimulant may be utilized, so long as the dosage of immunostimulant is sufficient to produce the desired result. A non-limiting example of dosages of immunostimulants that can be utilized in accordance with the present disclosure include those in a range of about 0.001 to about 100 mg/kg of body weight/day, depending on the method of administration.

In the same manner, the methods described herein above may thus include the step of administering an effective amount of an immunostimulant, wherein the immunostimulant is effective in significantly enhancing the immune response of the patient, and thereby allowing the immune system to mount a systemic attack on the pathogen-derived antigens. The immunostimulant may be administered at the same time as either the enzyme conjugate or the prodrug (if administered), or the immunostimulant may be administered before or after the administration of the enzyme conjugate (as well as before or after administration of the prodrug, when included in the method); in addition, the immunostimulant may be administered once or multiple times to the patient.

The compositions of the present disclosure (including the enzyme conjugates, prodrugs, immunostimulants, and/or other desired components) may be administered to a subject by any methods known in the art, including but not limited to, oral, topical, transdermal, parenteral, subcutaneous, intranasal, intramuscular, intraperitoneal, and intravenous routes, including both local and systemic applications. In addition, any of the compositions of the present disclosure may be designed to provide delayed and/or controlled release using formulation techniques which are well known in the art.

In one non-limiting embodiment, oral delivery of the enzyme conjugate can be administered using a dosage form (pill) that has been developed for injection of drugs directly into the small intestine (Imran, "Expert View: A Novel Approach to the Oral Delivery of Biologics, Peptides and Antibodies," *On Drug Delivery* (2016) 69:18-19).

Certain non-limiting embodiments of the present disclosure are also directed to a method of treating and/or purifying *Plasmodium*-infected blood. The method includes exposing the *Plasmodium*-infected blood to any of the enzyme conjugates disclosed or otherwise contemplated herein. The method may further include the step of exposing the *Plasmodium*-infected blood to any of the prodrugs disclosed or otherwise contemplated herein; when this step is performed, the method may further include the step of allowing unbound enzyme conjugate to be substantially cleared from the blood (or substantially clearing unbound enzyme conjugate from the blood) before exposing the blood to the prodrug.

The method of treating and/or purifying *Plasmodium*-infected blood may be performed in vivo, where the *Plasmodium*-infected blood is present in a subject. Alternatively, the method of treating and/or purifying *Plasmodium*-infected blood may be performed ex vivo. When the method is performed ex vivo, the method may simply involve treated a surface which has come into contact with *Plasmodium*-infected blood (i.e., a method of sanitizing a surface). Alternatively, the ex vivo method may be an ex vivo therapeutic method, where the *Plasmodium*-infected blood is removed from a subject prior to exposure to the enzyme conjugate; in this manner, the ex vivo therapeutic method may further include placing the treated blood back into the subject.

A particular (but non-limiting) embodiment of the present disclosure includes a method of purifying *Plasmodium*-infected blood ex vivo. In the method, *Plasmodium*-infected blood is removed from a subject. Any of the enzyme conjugates disclosed or otherwise contemplated herein is attached to a solid surface, and the *Plasmodium*-infected blood removed from the subject is passed over the solid surface in a manner that allows for the removal of infected erythrocytes from the *Plasmodium*-infected blood. The blood can then subsequently be recovered, and the number of infected erythrocytes present in the recovered blood is substantially reduced; in certain non-limiting embodiments, the blood is purified such that the infected erythrocytes are substantially removed therefrom.

One non-limiting example of a solid surface that may be utilized includes an affinity column. However, the present disclosure is not limited to this particular embodiment of solid surface. Indeed, many varied types of solid surfaces that can be utilized in cell removal/blood purification techniques are well known in the art, and thus, no further discussion related thereto is deemed necessary. In addition, in a particular (but non-limiting) embodiment, the method may further include the step of washing the solid surface with a reagent that binds to the *Plasmodium*-infected cells (such as, but not limited to, excess ligand that is the same or similar to the ligand present in the enzyme conjugate); in this manner, the cells can be removed from the solid surface such that the solid surface can be regenerated for multiple uses.

Certain non-limiting embodiments of the present disclosure also include a composition (such as, but not limited to, a pharmaceutical composition), wherein the composition comprises a therapeutically effective amount of any of the enzyme conjugate compositions described or otherwise contemplated herein, either alone or in combination with a pharmaceutically acceptable carrier. As used herein, a "pharmaceutically acceptable carrier" is a pharmaceutically acceptable solvent, suspending agent, or vehicle for delivering the enzyme conjugates to the human or animal. The carrier may be liquid or solid and is selected with the planned manner of administration in mind. Examples of pharmaceutically acceptable carriers that may be utilized in accordance with the present disclosure include, but are not limited to, PEG, liposomes, ethanol, DMSO, aqueous buffers (such as, but not limited to, phosphate buffered saline), oils, and combinations thereof. The compositions may be utilized, for example (but not by way of limitation), for treating a malarial infection in a subject and/or for treating/purifying *Plasmodium*-infected blood.

Certain non-limiting embodiments of the present disclosure also include a kit for use in treating a malarial infection in a subject, wherein the kit comprises at least one enzyme conjugate and at least one prodrug, wherein the enzyme conjugate and prodrug can be any of the enzyme conjugates and prodrugs disclosed or otherwise contemplated herein. In a particular (but non-limiting) embodiment, the kit further includes at least one of any of the immunostimulants disclosed or otherwise contemplated herein.

The compositions present in the kit may be provided in any form and in any amount (and/or concentration) that allows each of the compositions to function in accordance with the present disclosure. For example but not by way of limitation, each of the compositions may be provided in liquid form and disposed in bulk and/or single aliquot form within the kit. Alternatively (and/or in addition thereto), one or more of the compositions may be present in the kit in the form of a dry powder, such as a lyophilized powder, and the kit may further include excipient(s) for dissolution of the dried compositions; in this manner, a solution having the appropriate concentration(s) for administration to each individual subject can be obtained from these components. In addition, the kit can further include a set of written instructions explaining how to use the kit (including, for example but not by way of limitation, concentrations for administration to particular patient populations). A kit of this nature can be used when performing any of the methods described or otherwise contemplated herein, as well as any additional methods that may be envisioned by a person having ordinary skill in the art.

While the compositions, kits, and methods of the present disclosure have been described in terms of particular embodiments, it will be apparent to those of ordinary skill in the art that variations may be applied to the compositions, kits, and/or methods and in the steps or in the sequence of steps of the methods described herein without departing from the concept, spirit, and scope of the inventive concepts. All such similar substitutions and modifications apparent to those skilled in the art are deemed to be within the spirit, scope, and concept of the inventive concepts as described herein.

Examples

Examples are provided hereinbelow. However, the present disclosure is to be understood to not be limited in its application to the specific experimentation, results, and laboratory procedures disclosed herein after. Rather, the Examples are simply provided as one of various embodiments and are meant to be exemplary, not exhaustive.

In at least one embodiment, the present disclosure includes a fusion protein (conjugate) which contains a variant cystathione-γ-lyase (CGL) protein and an annexin (e.g., at its C-terminus), wherein the fusion protein has methioninase-γ-lyase activity and is nonimmunogenic. In one non-limiting embodiment, a variant mouse cystathione-γ-lyase protein having three amino acid substitutions (at positions 58, 118, and 338) and having methioninase-γ-lyase activity, is conjugated to annexin V (AV) to form a mouse variant cystathione-γ-lyase-annexin V (mouseCGL-AV) fusion protein. In another non-limiting embodiment, a variant human cystathione-γ-lyase (CGL) protein having three amino acid substitutions (at positions 59, 119, and 339) and having methioninase-γ-lyase activity, is conjugated to annexin V (AV) to form a human variant cystathione-γ-lyase-annexin V (humanCGL-AV) fusion protein. Therefore, in at least one embodiment, the variant CGL-AV (mCGL-AV) is human CGL-AV. A procedure for making the fusion protein (enzyme conjugate) is shown, in at least one embodiment, in U.S. Pat. No. 9,987,241.

The present disclosure shows that the variant CGL-AV fusion protein (enzyme conjugate) displayed significant activity against malaria parasites and resulted in increased survival of mice infected with the malaria parasite.

The variant CGL-based enzyme conjugate system has key advantages over traditional pharmaceuticals. First, the variant CGL enzyme is specifically targeted, using an annexin such as (but not limited to) annexin V, to cells infected with the malaria parasite, thus reducing or eliminating side effects of the treatment. As noted above, as the parasite destroys its host erythrocyte, the parasitized cell expresses PS on its surface. The enzyme conjugate binds to the surface of the parasite-infected cells and cuts off the supply of the amino acid methionine to the parasites, which is needed for viability by parasite cells since they are unable to synthesize methionine. Unlike healthy human cells, malaria parasites are unable to synthesize their own methionine in order to be viable, and they must actively acquire methionine by cannibalizing their host cell and through active transport from the plasma outside the cell. The enzyme conjugate causes methionine starvation of the parasite, thereby killing the parasite. The enzyme conjugate may be optionally administered with a prodrug (e.g., selenomethionine), which is converted to drug (e.g., methylselenol) by the enzyme conjugate at the site of the infected cell. The release of methylselenol by the conversion of selenomethionine creates radical oxygen species (ROS) that attack the parasitized cells. Thus, greater numbers of cells containing the parasites are killed by this two-pronged approach when the prodrug selenomethionine is administered. A second major advantage of the enzyme conjugate system disclosed herein is its ability to avoid drug resistance. There is documented drug resistance to all current antimalarial drugs. The mechanisms of drug resistance in the malaria parasite provide no protection from the radical oxygen species generated by the variant CGL enzyme. Additionally, the ABC transport proteins in malaria (such as MDR1) actively contribute to annexin V binding by translocating PS to the cell surface. Increasing drug resistance also increases the exposure of PS, thus driving greater accumulation of the variant CGL enzyme conjugate on the surface of infected cells. This enzyme conjugate treatment system thus represents a new type of malarial treatment that specifically destroys infected cells with minimal or no side effects. Additionally, the presently disclosed system can be used to treat viral and bacterial pathogens which express PS, such as HIV (which causes AIDS) and tuberculosis.

Experimental

Figure 1:
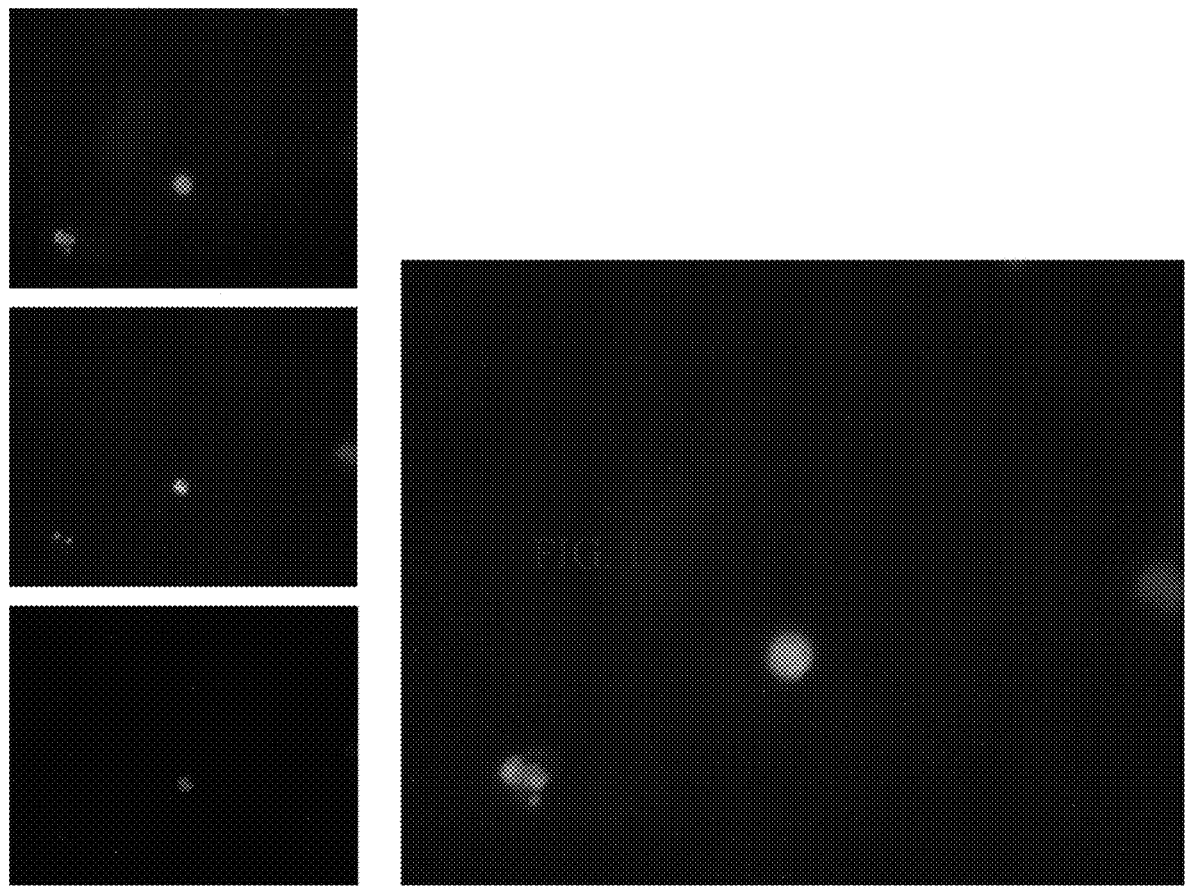
FIG. 1 shows micrographs of blood from mice infected with the murine parasite *P. yoelii*. Blood samples were incubated with the fusion protein mutant cystathione-γ-lyase-annexin V (mCGL-AV), also referred to herein as methexin, tagged with a green fluorescent marker. Cell membranes were stained red (top left), DNA was stained blue (center left), and the fusion protein was stained green (bottom left). The compound image (right) shows that the fusion protein localizes to the infected cell near the center of the image. However, the protein does not localize to the eosinophil (displaying a signature headphone shaped granule) located in the bottom left of all images. Other data (not shown) has indicated that the fusion protein does not bind to healthy blood cells.

The localization of mCGL-AV to murine erythrocytes infected with a murine *Plasmodium* parasite was confirmed with florescent light microscopy (FIG. 1). The fluorescently tagged fusion protein mCGL-AV selectively bound infected red blood cells. The fusion protein did not bind healthy erythrocytes or peripheral blood leukocytes. This confirms that the fusion protein is actively homing in on infected cells. The localization of a high concentration of fusion protein to infected cells minimizes the necessary dose of fusion protein and guarantees the selective destruction of parasites.

Figure 2:
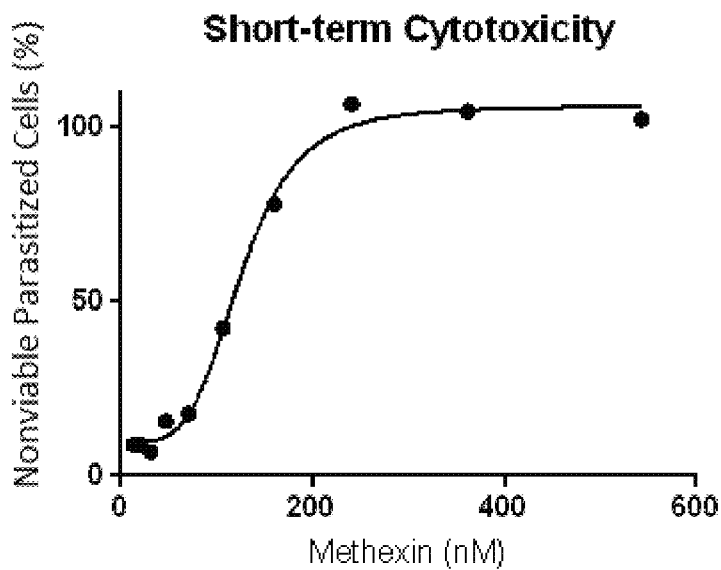
FIG. 2 shows that the fusion protein mCGL-AV has potent antimalarial properties and initiates damage in parasitized cells (erythrocytes with parasites) in a short time period at concentrations <1 µM. Blood was harvested and pooled from three mice infected with the murine *Plasmodium* parasite *P. yoelii*. Pooled blood parasitemia was 4.0%. Erythrocytes were extracted from the blood and washed to remove debris. The blood was then incubated with varying concentrations of mCGL-AV (methexin) for 3 hours. The blood was then washed to remove excess protein and debris. The treated blood was stained with propidium iodide to reveal the presence of nonviable cells, and nonviable cells were enumerated via flow cytometry. The number of nonviable cells is expressed as a percentage of the total number of parasitized cells.

To confirm that the localized protein can destroy malarial parasites, mouse blood containing the murine parasite *P. yoelii* was harvested and incubated with mCGL-AV. Following a 3 hour incubation, the number erythrocytes with damaged plasma membranes (thus rendering the erythrocytes nonviable) and containing parasites was enumerated with flow cytometry using propidium iodide (PI) staining. Propidium iodide binds the DNA of parasites in erythrocytes with damaged membranes but is unable to cross the plasma membrane of healthy cells. Healthy erythrocytes do not contain DNA. Therefore, cells stained by propidium iodide must have a nucleus (containing DNA) and a damaged membrane and thus are not viable. In this short term 3 hour test with blood containing a low percentage of erythrocytes containing parasites (4%), when the concentration of mCGL-AV (methexin) reached 300 nM, 100% of erythrocytes containing parasites were nonviable (FIG. 2).

Figure 3:
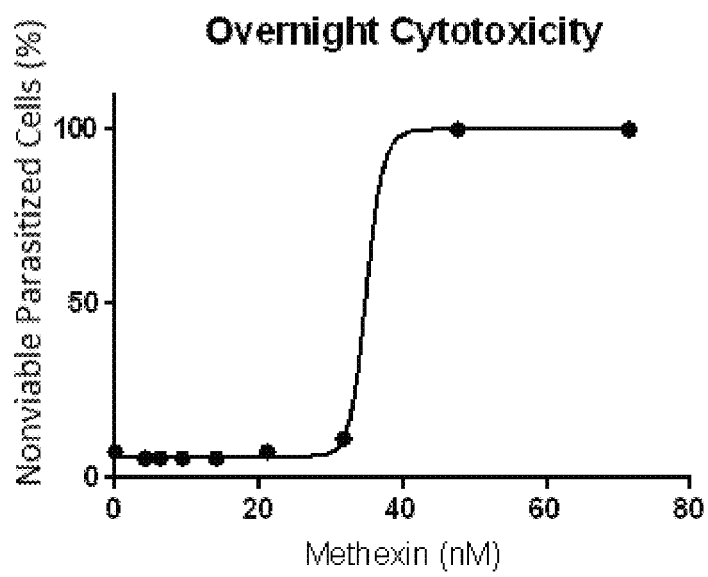
FIG. 3 shows that when erythrocytes containing parasites were incubated overnight with mCGL-AV, the parasitized cells showed an increasing sensitivity towards the fusion protein at concentrations <0.1 µM. Blood was harvested and pooled from three mice infected with the murine *Plasmo-*

In addition to possessing rapid antimalarial properties, mCGL-AV has longer term parasite-specific cytotoxic effects. Blood with a low percentage of erythrocytes containing parasites (4%) was harvested from several animals and pooled. The blood was incubated for several hours with varying concentrations of mCGL-AV. After incubation, the red blood cells were thoroughly washed to remove debris and excess fusion protein. Then the red blood cells were cultured overnight. These overnight cultures show that mCGL-AV has a dosage dependent cytotoxic effect on malarial parasites at remarkably low concentrations (FIG. 3). This activity was confirmed in two murine malarial parasite cell lines: *P. yoelii* and *P. berghei*. Traditionally, antimalarial agents are considered promising when they have antimalarial activity at micromolar concentrations. Advantageously, the fusion prodrug mCGL-AV has activity at nanomolar concentrations.

In a demonstration of the effect of mCGL-AV on a much worse case of malaria, hyperparasitized mouse blood was collected and incubated for a short period of time with fusion protein (FIG. 4). In the case of hyperparasitized blood, where greater than 20% of all cells were infected with malaria, a short incubation with excess mCGL-AV (1.6 µM) resulted in the almost complete elimination of malarial parasites. To insure that healthy red blood cells were not damaged by such high concentrations of mCGL-AV, samples of treated and untreated blood were imaged using light microscopy to search for signs of hemolysis. After 3 hours of incubation, no significant hemolysis was observed (FIG. 5). Further, the addition of the exogenous mCGL-AV substrate selenomethionine to overnight cultures boosted the cytotoxicity of the fusion protein by serving as a source for the production of ROS (FIG. 6).

The administration of the mCGL-AV fusion protein in mice has been shown to be well tolerated for as long as 3 weeks with daily injections of 10 mg/kg. mCGL-AV has been shown to be effective in increasing survival of mice infected with a malarial parasite. FIG. 7 shows survival in mice treated with mCGL-AV ("enzyme"). The mCGL-AV was assayed for antimalarial activity in a mouse model of malaria. In each group (n=7), 8 week old CF-1 mice were inoculated with the parasite *P. berghei*. The following day mice in the treated group received an i.p. injection of 10 mg/kg mCGL-AV. This single dose resulted in a significant increase in survival, and resulted in a complete cure in 3 of 7 mice treated with mCGL-AV. All untreated mice perished within 10 days. Surviving treated mice were euthanized for histology at day 30, and no parasites were detected at that time.

The cytotoxicity of the mCGL-AV fusion protein was assayed over a period of one month in healthy mice receiving daily injections of 10 mg/kg fusion protein for a period of 20 days. No drug related side effects were observed in treated mice. Additionally, there were no significant weight differences (FIG. 8) between treated and untreated mice. Furthermore, necropsy and histological examination of target organs at the conclusion of the study revealed no organ specific drug toxicity.

At the conclusion of the treatment period, mice were sacrificed for tissue analysis. Target organs including kidneys, liver, spleen, heart, lungs, and testes were removed and fixed in 10% neutral buffered formalin for 24 hours. Organs were then sliced to appropriate size and orientated in cassettes for paraffin embedding and fixation by the Tissue Pathology Core of the Stephenson Cancer Center at the University of Oklahoma Health Sciences Center. Hematoxylin and eosin stained sections were produced by the Tissue pathology Core for evaluation of organ cytotoxicity. Slides were viewed on a Nikon Eclipse E800 compound microscope, and whole slide images were collected using a Sony Exmore CMOS camera. Slides from treated mice were compared to control slides from healthy animals to detect organ cytotoxicity.

Blood samples from infected mice were stained according to a modified Giemsa staining procedure. Infected blood was harvested from the lateral tail vein of infected mice, and 25 µL was used to create a blood smear. Samples were allowed to air-dry before fixing in ice-cold methanol for 30 seconds. Fixed samples were then stained in a 5% v/v solution of Giemsa stain and tap water. Samples were then rinsed, and the number of parasites was analyzed by oil immersion microscopy. Histological examination of blood samples from infected mice confirmed the effect of the mCGL-AV on the relative numbers of parasites (FIG. 9). A single dose of 10 mg/kg of mCGL-AV 24 hours after parasite inoculation drastically decreased the number of parasites (FIG. 9, left panel) compared to untreated controls in mice (FIG. 9, right panel).

In a demonstration of the effect of mCGL-AV on a bacterial model, the activity of the mCGL-AV was assayed in an in vitro model of bacterial infection. Mouse derived mesenchymal stem cells were seeded into a 96 well microtiter plate at a density of $5 \times 10^5$ cells per well and allowed to rest for 24 hours. Cells were then inoculated with $10^6$ CFU of pathogenic *Haemophilus influenzae* and then centrifuged at 1000 g for 10 minutes at 4° C. to promote cellular uptake of the bacteria. The cultures were then rinsed with Hank's balanced salt solution and incubated with 75 µg/mL gentamicin for 3 hours to destroy extracellular bacteria. Cultures were then treated with 500 µM of fusion protein for 36 hours in antibiotic free medium. After treatment, cells were harvested using 0.25% trypsin-EDTA and lysed to release bacteria. Bacteria were then plated on chocolate agar plates, and the number of viable bacteria was determined by colony counting. FIG. 10 shows that the number of viable bacteria (CFUs) was significantly reduced in cultures treated with mCGL-AV.

Stability of the mCGL-AV fusion protein was assayed at 4° C., 25° C., and 37° C. over a period of one month. Samples were taken, and enzyme stability was assayed using a colorimetric enzyme activity assay. Dilutions of enzyme were incubated with L-methionine for 10 minutes at 37° C. to catalyze the production of α-ketobutyrate. Trichloroacetic acid (50A % w/v) was used to terminate the enzymatic reaction, followed by 2 minutes of centrifugation at 15000×g to remove debris. The supernatant was added to sodium acetate pH buffer, and 0.1% 3-methyl-2-benzo-thiazolinone hydrazone hydrochloride hydrate colorimetric indicator was added for color development. Development proceeded for 30 minutes at 50° C. in a Thermo Fisher Isotemp incubator. Absorbance was read in a microtiter plate at 320 nm. Samples from various time points were compared to control samples of fresh enzyme. FIG. 11 shows that the mCGL-AV fusion protein retained significant activity after one month when stored at room temperature or refrigerated.

Thus, in accordance with the present disclosure, there have been provided enzyme conjugate compositions, as well as kits containing same and methods of producing and utilizing same, that fully satisfy the objectives and advantages set forth hereinabove. Although embodiments of the present disclosure have been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure. Changes may thus be made in the formulation of the various components and compositions described herein, the methods described herein or in the steps or the sequence of steps of the methods described herein without departing from the spirit and scope of the present disclosure.

What is claimed is:

1. A method of killing a *Plasmodium*-infected erythrocyte in a subject in need of such therapy, comprising:
administering to the subject an effective amount of an enzyme conjugate comprising a variant cystathione-gamma-lyase (CGL) enzyme conjugated to an annexin ligand, wherein the variant CGL enzyme has L-methioninase activity and has an amino acid sequence that is at least about 95% identical to the amino acid sequence of SEQ ID NO:2 and has substitutions in positions 59, 119, and 339 thereof, or is at least about 95% identical to the amino acid sequence of SEQ ID NO:1 and has substitutions in positions 58, 118, and 338 thereof, and wherein the annexin ligand has the ability to specifically and stably bind to phosphatidylserine (PS) present on an outer surface of the *Plasmodium*-infected erythrocyte such that the enzyme conjugate is maintained on the outer surface of the infected erythrocyte with substantially no internalization of the enzyme conjugate by the infected erythrocyte, wherein the PS is not present on an outer surface of an uninfected healthy erythrocyte, and wherein the enzyme conjugate is administered absent concurrent therapy with a prodrug acted on by the enzyme conjugate.

2. The method of claim 1, wherein the variant CGL enzyme of the enzyme conjugate comprises an amino acid sequence comprising SEQ ID NO:3 or SEQ ID NO:4.

3. The method of claim 1, wherein the annexin ligand is annexin V.

4. The method of claim 1, wherein the variant CGL enzyme and the annexin ligand are directly coupled together.

5. The method of claim 1, wherein the variant CGL enzyme and the annexin ligand are indirectly coupled together via a linker molecule.

6. The method of claim 1, wherein the enzyme conjugate further comprises a polyethylene glycol (PEG) molecule.

7. The method of claim 1, further comprising the step of administering an effective amount of an immunostimulant to the subject.

8. A method of killing a *Plasmodium*-infected erythrocyte in *Plasmodium*-infected blood, comprising:

adding to the *Plasmodium*-infected blood an enzyme conjugate comprising a variant cystathione-gamma-lyase (CGL) enzyme conjugated to an annexin ligand, wherein the variant CGL enzyme has L-methioninase activity and has an amino acid sequence that is at least about 95% identical to the amino acid sequence of SEQ ID NO: 2 and has substitutions in positions 59, 119, and 339 thereof, or is at least about 95% identical to the amino acid sequence of SEQ ID NO: 1 and has substitutions in positions 58, 118, and 338 thereof, and wherein the annexin ligand has the ability to specifically and stably bind to phosphatidylserine (PS) present on an outer surface of the *Plasmodium*-infected erythrocyte such that the enzyme conjugate is maintained on the outer surface of the infected erythrocyte with substantially no internalization of the enzyme conjugate by the infected erythrocyte, wherein the PS is not present on an outer surface of an uninfected healthy erythrocyte, and wherein the *Plasmodium*-infected blood is exposed to the enzyme conjugate in the absence of a prodrug acted on by the enzyme conjugate.

9. The method of claim 8, wherein the annexin ligand is annexin V.

10. The method of claim 8, wherein the variant CGL enzyme and the annexin ligand are directly coupled together.

11. The method of claim 8, wherein the variant CGL enzyme and the annexin ligand are indirectly coupled together via a linker molecule.

12. The method of claim 8, wherein the enzyme conjugate further comprises a polyethylene glycol (PEG) molecule.

13. The method of claim 8, further comprising the step of adding an effective amount of an immunostimulant to the *Plasmodium*-inf